(12) United States Patent
Ogawa et al.

(10) Patent No.: US 10,620,425 B2
(45) Date of Patent: Apr. 14, 2020

(54) MEASUREMENT APPARATUS AND METHOD OF OPERATING MEASUREMENT APPARATUS

(71) Applicant: OLYMPUS CORPORATION, Tokyo (JP)

(72) Inventors: Kiyotomi Ogawa, Tokyo (JP); Naoki Yamamoto, Tokyo (JP); Toshiyuki Noguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/114,449

(22) Filed: Aug. 28, 2018

(65) Prior Publication Data

US 2019/0064499 A1 Feb. 28, 2019

(30) Foreign Application Priority Data

Aug. 31, 2017 (JP) .................................. 2017-167055

(51) Int. Cl.
*G02B 23/24* (2006.01)
*G02B 27/10* (2006.01)
(Continued)

(52) U.S. Cl.
CPC ........ *G02B 23/243* (2013.01); *A61B 1/00006* (2013.01); *A61B 1/00009* (2013.01); *A61B 1/00039* (2013.01); *A61B 1/00059* (2013.01); *A61B 1/00096* (2013.01); *A61B 1/00186* (2013.01); *A61B 1/04* (2013.01); *A61B 1/0638* (2013.01); *A61B 1/0646* (2013.01); *A61B 1/0669* (2013.01); *A61B 1/07* (2013.01); *G02B 23/2469* (2013.01); *G02B 23/2484* (2013.01); (Continued)

(58) Field of Classification Search
None
See application file for complete search history.

(56) References Cited

U.S. PATENT DOCUMENTS 5,187,572 A * 2/1993 Nakamura ......... A61B 1/00009
348/164
5,434,669 A * 7/1995 Tabata ................... A61B 1/042
356/241.5

(Continued)

FOREIGN PATENT DOCUMENTS

JP 2013044806 A 3/2013

*Primary Examiner* — Kate H Luo
(74) *Attorney, Agent, or Firm* — Scully, Scott, Murphy & Presser, P.C.

(57) ABSTRACT

In a measurement apparatus, a first pupil is capable of transmitting first light of a first wavelength band, and a second pupil is capable of transmitting second light of a second wavelength band. An imaging device includes a plurality of first pixels generating first pixel signals based on third light of a third wavelength band transmitted through a first optical filter that is capable of transmitting the third light. The imaging device further includes a plurality of second pixels generating second pixel signals based on fourth light of a fourth wavelength band transmitted through a second optical filter that is capable of transmitting the fourth light. A light source outputs illumination light including only fifth light of a fifth wavelength band and sixth light of a sixth wavelength band not overlapping the fifth wavelength band.

8 Claims, 17 Drawing Sheets

(51) Int. Cl.
   *H04N 5/225*    (2006.01)
   *A61B 1/04*     (2006.01)
   *A61B 1/06*     (2006.01)
   *A61B 1/07*     (2006.01)
   *A61B 1/00*     (2006.01)

(52) U.S. Cl.
   CPC ....... *G02B 27/1013* (2013.01); *H04N 5/2253* (2013.01); *A61B 1/00045* (2013.01); *H04N 2005/2255* (2013.01)

(56) References Cited

U.S. PATENT DOCUMENTS

| | | | | |
|---|---|---|---|---|
| 2003/0040668 | A1* | 2/2003 | Kaneko | A61B 1/00096 600/407 |
| 2005/0234302 | A1* | 10/2005 | MacKinnon | A61B 1/00186 600/181 |
| 2006/0241496 | A1* | 10/2006 | Fengler | A61B 1/00009 600/476 |
| 2009/0312607 | A1* | 12/2009 | Sunagawa | A61B 1/0638 600/160 |
| 2018/0092516 | A1* | 4/2018 | Imade | A61B 1/00006 |

\* cited by examiner

FIG. 9

| R_00 | Gr_01 | R_02 | Gr_03 |
|------|-------|------|-------|
| Gb_10 | B_11 | Gb_12 | B_13 |
| R_20 | Gr_21 | R_22 | Gr_23 |
| Gb_30 | B_31 | Gb_32 | B_33 |

FIG. 10

| R_00-OB | R_00-OB | R_02-OB | R_02-OB |
|---------|---------|---------|---------|
| R_00-OB | R_00-OB | R_02-OB | R_02-OB |
| R_20-OB | R_20-OB | R_22-OB | R_22-OB |
| R_20-OB | R_20-OB | R_22-OB | R_22-OB |

FIG. 11

| Gr_01 -OB | Gr_01 -OB | Gr_03 -OB | Gr_03 -OB |
|---|---|---|---|
| Gb_10 -OB | Gb_10 -OB | Gb_12 -OB | Gb_12 -OB |
| Gr_21 -OB | Gr_21 -OB | Gr_23 -OB | Gr_23 -OB |
| Gb_30 -OB | Gb_30 -OB | Gb_32 -OB | Gb_32 -OB |

FIG. 12

| B_11 -OB | B_11 -OB | B_13 -OB | B_13 -OB |
|---|---|---|---|
| B_11 -OB | B_11 -OB | B_13 -OB | B_13 -OB |
| B_31 -OB | B_31 -OB | B_33 -OB | B_33 -OB |
| B_31 -OB | B_31 -OB | B_33 -OB | B_33 -OB |

MEASUREMENT APPARATUS AND METHOD OF OPERATING MEASUREMENT APPARATUS

BACKGROUND OF THE INVENTION

Field of the Invention

The present invention relates to a measurement apparatus and a method of operating a measurement apparatus.

Priority is claimed on Japanese Patent Application No. 2017-167055, filed on Aug. 31, 2017, the content of which is incorporated herein by reference.

Description of Related Art

In imaging apparatuses of recent years, imaging devices including color filters of the primary colors consisting of red (R), green (G), and blue (B) have been widely used. When the transmission wavelength band of a color filter becomes larger, the amount of transmitted light increases, and the imaging sensitivity increases. For this reason, in a general imaging device, a technology of intentionally causing the transmittance wavelength characteristics of R, G, and B color filters to overlap is used.

In a phase difference AF or the like, a phase difference based on a parallax between two pupils is measured. For example, in Japanese Unexamined Patent Application, First Publication No. 2013-044806, an imaging apparatus including a pupil division optical system having a first pupil area transmitting R and G light and a second pupil area transmitting G and B light is disclosed. An R image and a B image are extracted from a Bayer image acquired by an imaging device mounted in the imaging apparatus. A phase difference is detected on the basis of a positional deviation between an R image corresponding to the first pupil area and a B image corresponding to the second pupil area.

In a case in which the degree of color separation between a plurality of color filters disposed in the imaging device is low, crosstalk occurs between the R image and the B image. In other words, the R image includes a B component based on light transmitted through the second pupil area, and the B image includes an R component based on light transmitted through the first pupil area. Due to this crosstalk, the error included in the detected phase difference, in other words, the measurement error increases. The imaging apparatus disclosed in Japanese Unexamined Patent Application, First Publication No. 2013-044806 performs a crosstalk reducing process of correcting pixel values of the R image and the B image on the basis of pixel values of the G image. In this way, the influence of crosstalk can be reduced in this imaging apparatus.

SUMMARY OF THE INVENTION

According to a first aspect of the present invention, a measurement apparatus includes an observation optical system, an imaging device, a light source, an image acquiring unit, and a measurement unit. The observation optical system includes a first pupil and a second pupil. The first pupil is capable of transmitting first light of a first wavelength band. The second pupil is capable of transmitting second light of a second wavelength band different from the first wavelength band. The imaging device is disposed at a position at which light transmitted through the observation optical system is incident and includes a plurality of first pixels and a plurality of second pixels. The plurality of first pixels generate first pixel signals based on third light of a third wavelength band transmitted through a first optical filter that is capable of transmitting the third light. The plurality of second pixels generate second pixel signals based on fourth light of a fourth wavelength band transmitted through a second optical filter that is capable of transmitting the fourth light. The fourth wavelength band is different from the third wavelength band. The light source outputs illumination light including only fifth light of a fifth wavelength band and sixth light of a sixth wavelength band not overlapping the fifth wavelength band. The image acquiring unit acquires a first image based on the first pixel signals and a second image based on the second pixel signals from a captured image based on the first pixel signals and the second pixel signals. The measurement unit measuring a phase difference between the first image and the second image. At least a part of the first wavelength band and at least a part of the third wavelength band overlap each other. At least a part of the first wavelength band and at least a part of the fifth wavelength band overlap each other. At least a part of the fifth wavelength band and at least a part of the third wavelength band overlap each other. The first wavelength band and the sixth wavelength band do not overlap each other. At least a part of the second wavelength band and at least a part of the fourth wavelength band overlap each other. At least a part of the second wavelength band and at least a part of the sixth wavelength band overlap each other. At least a part of the sixth wavelength band and at least a part of the fourth wavelength band overlap each other. The second wavelength band and the fifth wavelength band do not overlap each other.

According to a second aspect of the present invention, in the first aspect, the measurement apparatus may further include a light source control unit setting a state of the light source to one of a first state and a second state. The light source may output first illumination light including only the fifth light and the sixth light when the first state is set in the light source. The light source may output second illumination light including only one of the fifth light and the sixth light when the second state is set in the light source. Only one of the first image and the second image may be output to a display unit when the second state is set in the light source.

According to a third aspect of the present invention, in the first aspect, the measurement apparatus may further include a light source control unit controlling light intensities of the fifth light and the sixth light on the basis of a degree of difference in brightness between the first image and the second image.

According to a fourth aspect of the present invention, in the first aspect, the observation optical system may be constituted as a monocular optical system and include a pupil filter. The pupil filter may include a transparent flat plate, a thin film, the first pupil, and the second pupil. The thin film may be disposed on a surface of the flat plate and have a first opening portion and a second opening portion formed therein. The first pupil may be constituted by a third optical filter disposed at the first opening portion and transmit the first light. The second pupil may be constituted by a fourth optical filter disposed at the second opening portion and transmit the second light.

According to a fifth aspect of the present invention, in the first aspect, the light source may include one or more first light emitting devices generating the fifth light and one or more second light emitting devices generating the sixth light.

According to a sixth aspect of the present invention, in the fifth aspect, the measurement apparatus may further include an illumination optical system emitting the illumination light supplied from the light source to a subject. The light source may further include an optical mixing unit that mixes the fifth light supplied from the first light emitting device and the sixth light supplied from the second light emitting device and outputs the illumination light including the fifth light and the sixth light that are mixed.

According to a seventh aspect of the present invention, in the sixth aspect, the measurement apparatus may further include an insertion part to be inserted into the subject. The illumination optical system may include a light transmitting unit transferring the illumination light supplied from the optical mixing unit to a tip end of the insertion part.

According to an eighth aspect of the present invention, in the first aspect, the measurement apparatus may further include an illumination optical system emitting the illumination light supplied from the light source to a subject. The illumination optical system may include an optical mixing unit that mixes the fifth light supplied from the light source and the sixth light supplied from the light source.

According to a ninth aspect of the present invention, in the eighth aspect, the measurement apparatus may further include an insertion part to be inserted into the subject. The illumination optical system may further include a light transmitting unit that transfers the illumination light supplied from the optical mixing unit to a tip end of the insertion part.

According to a tenth aspect of the present invention, a method of operating a measurement apparatus includes an image acquisition step and a measurement step. The measurement apparatus includes: an observation optical system; an imaging device; and a light source. The observation optical system includes a first pupil and a second pupil. The first pupil is capable of transmitting first light of a first wavelength band. The second pupil is capable of transmitting second light of a second wavelength band different from the first wavelength band. The imaging device is disposed at a position at which light transmitted through the observation optical system is incident and includes a plurality of first pixels and a plurality of second pixels. The plurality of first pixels generate first pixel signals based on third light of a third wavelength band transmitted through a first optical filter that is capable of transmitting the third light. The plurality of second pixels generate second pixel signals based on fourth light of a fourth wavelength band transmitted through a second optical filter that is capable of transmitting the fourth light. The fourth wavelength band is different from the third wavelength band. The light source outputs illumination light including only fifth light of a fifth wavelength band and sixth light of a sixth wavelength band not overlapping the fifth wavelength band. In the image acquisition step, the measurement apparatus acquires a first image based on the first pixel signals and a second image based on the second pixel signals from a captured image based on the first pixel signals and the second pixel signals. In the measurement step, the measurement apparatus measures a phase difference between the first image and the second image. At least a part of the first wavelength band and at least a part of the third wavelength band overlap each other. At least a part of the first wavelength band and at least a part of the fifth wavelength band overlap each other. At least a part of the fifth wavelength band and at least a part of the third wavelength band overlap each other. The first wavelength band and the sixth wavelength band do not overlap each other. At least a part of the second wavelength band and at least a part of the fourth wavelength band overlap each other. At least a part of the second wavelength band and at least a part of the sixth wavelength band overlap each other. At least a part of the sixth wavelength band and at least a part of the fourth wavelength band overlap each other, and the second wavelength band and the fifth wavelength band do not overlap each other.

BRIEF DESCRIPTION OF THE DRAWINGS

FIG. 9 is a diagram showing the pixel arrangement of a Bayer image according to the first embodiment of the present invention;

FIG. 10 is a diagram showing the pixel arrangement of an R image according to the first embodiment of the present invention;

FIG. 11 is a diagram showing the pixel arrangement of a G image according to the first embodiment of the present invention;

FIG. 12 is a diagram showing the pixel arrangement of a B image according to the first embodiment of the present invention;

DETAILED DESCRIPTION OF THE INVENTION

Hereinafter, embodiments of the present invention will be described with reference to the drawings. Hereinafter, a measurement endoscope apparatus that is one example of a measurement apparatus will be described. The measurement apparatus may be a digital still camera, a video camera, a mobile phone equipped with a camera, a mobile information terminal equipped with a camera, a personal computer equipped with a camera, a monitoring camera, a digital microscope, or the like.

First Embodiment

Figure 1:
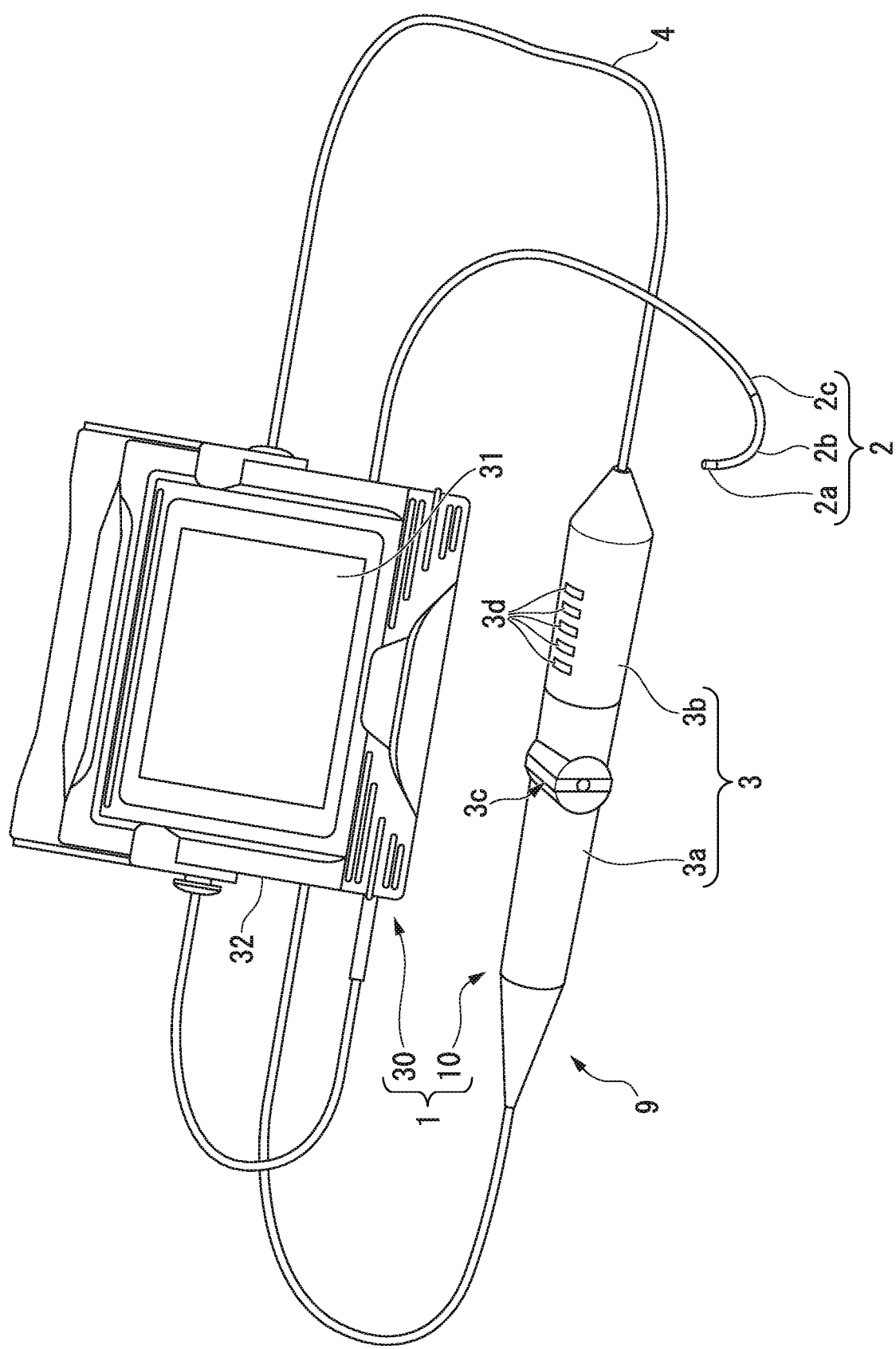
FIG. 1 is a diagram showing the entire configuration of a measurement apparatus according to a first embodiment of the present invention.

FIG. 1 shows the entire configuration of a measurement apparatus 1 according to a first embodiment of the present invention. As shown in FIG. 1, the measurement apparatus 1 includes an endoscope 10 and an apparatus main body 30. The endoscope 10 includes a long and thin insertion part 2 and an operation unit 3. The apparatus main body 30 and the endoscope 10 are connected using a universal cord 4 extending from the operation unit 3.

The insertion part 2 is inserted into a subject that is a target for observation or measurement. The insertion part 2 includes a tip end portion 2a, a bending portion 2b, and a flexible tube portion 2c. The tip end portion 2a is disposed at a tip end of the insertion part 2. The bending portion 2b is configured to be bent in a plurality of different directions. The flexible tube portion 2c has flexibility and is connected to the operation unit 3.

The operation unit 3 includes a bending operation part 3a and a button operation part 3b. The insertion part 2 and the bending operation part 3a constitute a scope unit 9. Mounting of the bending operation part 3a on the button operation part 3b and extraction of the bending operation part 3a from the button operation part 3b can be performed. In other words, the scope unit 9 is configured to be replaceable. For example, the scope unit 9 is one of a measurement scope unit and an observation scope unit. A lever 3c is disposed in the bending operation part 3a. A user can bend the bending portion 2b by operating the lever 3c. A plurality of switches 3d are disposed in the button operation part 3b. A user can control an imaging operation and the like using the measurement apparatus 1 by operating the switches 3d. As will be described later, a light source is disposed inside the button operation part 3b.

A display unit 31 is disposed on the surface of a casing 32 of the apparatus main body 30. An image processing circuit, a control circuit, and the like are disposed inside the casing 32 of the apparatus main body 30.

Figure 2:
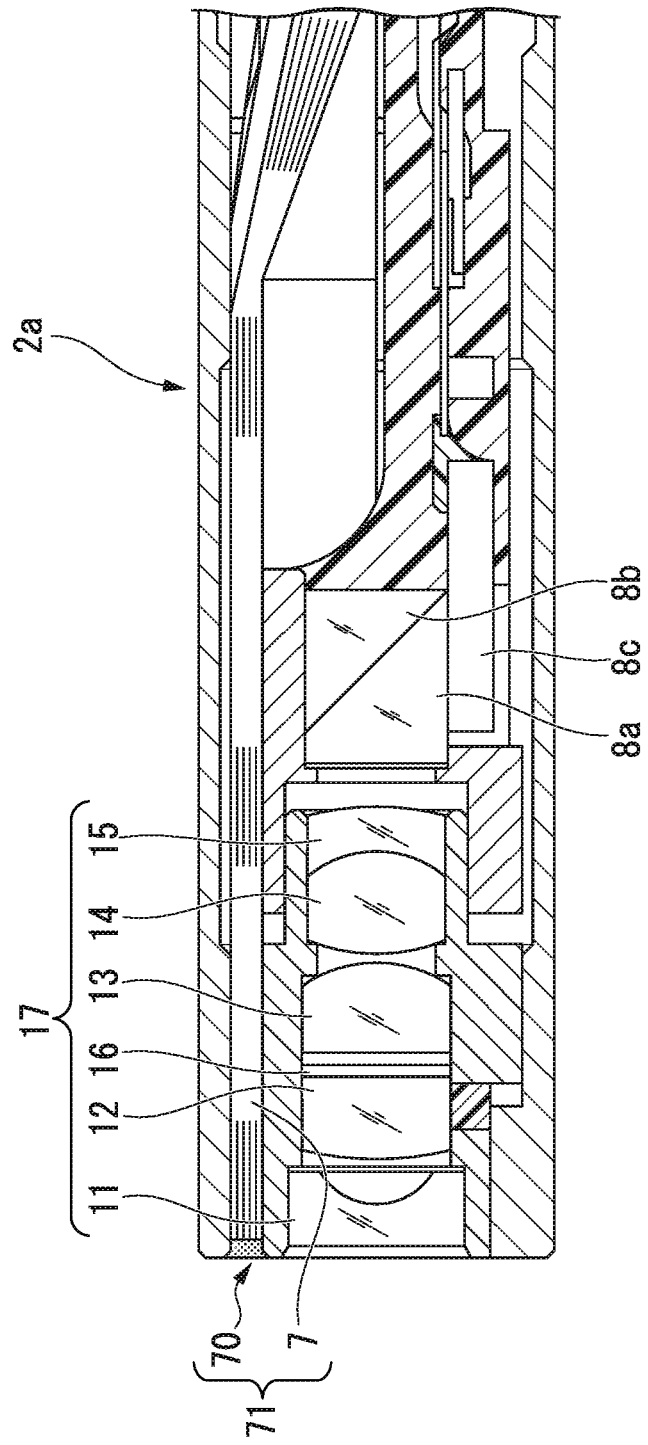
FIG. 2 is a cross-sectional view of a tip end portion of an insertion part included in the measurement apparatus according to the first embodiment of the present invention.

FIG. 2 shows the structure of the tip end portion 2a of the measurement scope unit. In FIG. 2, a cross-section including a center axis of the tip end portion 2a is shown. The light guide 7 is disposed inside the insertion part 2 and the bending operation part 3a. For example, the light guide 7 is a bundle of a plurality of optical fibers. The light guide 7 transfers illumination light from the light source disposed inside the button operation part 3b to the tip end portion 2a. An illumination window 70 and a lens 11 are disposed on a tip end face of the tip end portion 2a. The illumination window 70 is connected to the light guide 7. The illumination window 70 outputs the illumination light output from the light guide 7 to the outside of the tip end portion 2a. The light guide 7 and the illumination window 70 constitute an illumination optical system 71 that emits illumination light from the light source to a subject. Reflected light of the illumination light emitted to the subject is incident to the lens 11.

The lens 11, a lens 12, a lens 13, a lens 14, and a lens 15 are disposed inside the tip end portion 2a. Optical axes of such lenses coincide with each other. A pupil filter 16 is disposed between the lens 12 and the lens 13. The pupil filter 16 includes two pupils. The pupil filter 16 forms light of two images having different viewpoints by dividing light supplied from a subject into two light fluxes of different colors. The lenses 11 to 15 and the pupil filter 16 constitute an observation optical system 17 that forms an image of light supplied from a subject in the imaging device 8c inside the tip end portion 2a. The observation optical system 17 is constituted as a monocular optical system in which optical axes of a plurality of lenses included therein approximately coincide with each other. In the observation scope unit, the pupil filter 16 includes one pupil that transmits light from a subject as it is.

A prism 8a, a protection member 8b, and an imaging device 8c (an imager; an image sensor) are disposed inside the tip end portion 2a. The prism 8a reflects light transmitted through the lens 15 in a direction of the imaging device 8c. Light incident to the prism 8a is reflected on a reflection face of the prism 8a and is incident to an imaging face of the imaging device 8c. The protection member 8b is bonded to the reflection face of the prism 8a. The prism 8a is fixed to the tip end portion 2a using the protection member 8b.

Figure 3A:
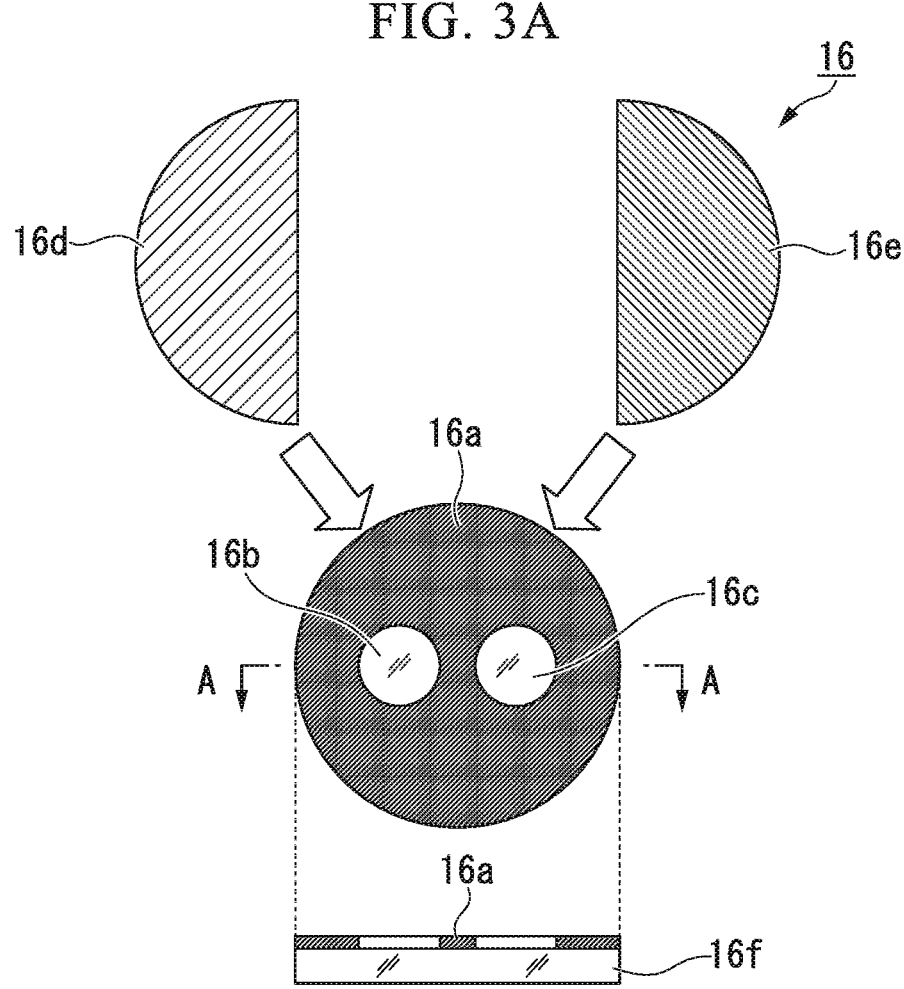
FIGS. 3A and 3B are diagrams showing the configuration of a pupil filter included in the measurement apparatus according to the first embodiment of the present invention.
Figure 3B:
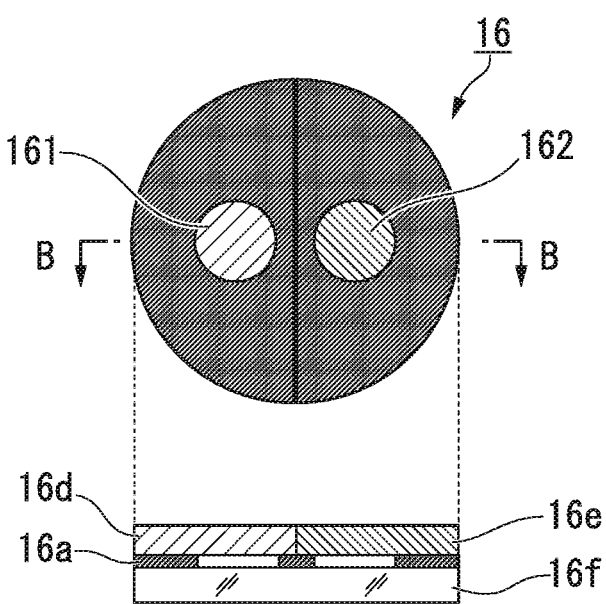

FIGS. 3A and 3B show the configuration of the pupil filter 16. In FIGS. 3A and 3B, the configuration of the pupil filter 16 when the pupil filter 16 is seen in a direction parallel to optical axes of the lens 11 to 15 is schematically shown. As shown in FIG. 3A, a thin film 16a is formed on the surface of a transparent flat plate 16f, and a first opening portion 16b and a second opening portion 16c are formed in the thin film 16a. For example, the flat plate 16f has a circular shape. The thin film 16a is a black metal such as black chromium. The thin film 16a is formed by vapor deposition or the like. The radiuses of the first opening portion 16b and the second opening portion 16c are the same. However, the radiuses of the first opening portion 16b and the second opening portion 16c may be different from each other. On the lower side in FIG. 3A, a cross-section A-A is shown which passes through the center of the flat plate 16f, the opening portion 16b, and the opening portion 16c for the flat plate 16f having the thin film 16a formed on the surface thereof.

A first color filter 16d having a half-circle shape and a second color filter 16e having a half-circle shape are attached to the surface of the thin film 16a. The first color filter 16d covers the first opening portion 16b, and the second color filter 16e covers the second opening portion 16c. Reflected light of illumination light emitted to a subject is incident to the first color filter 16d and the second color filter 16e. The first color filter 16d transmits red light and green light. The second color filter 16e transmits blue light and green light. As shown in FIG. 3B, the first color filter 16d disposed in the first opening portion 16b constitutes a first pupil 161, and the second color filter 16e disposed in the second opening portion 16c constitutes a second pupil 162. The pupil filter 16 functions as an aperture stop of the observation optical system 17. On the lower side in FIG. 3B, a cross-section B-B is shown which passes through the center of the flat plate 16f, the opening portion 16b, and the opening portion 16c for the flat plate 16f having the thin film 16a formed on the surface, the first color filter 16d, and the second color filter 16e.

Each of the first color filter 16d and the second color filter 16e is an interference filter in which thin films of multiple layers having different refractive indexes are deposited. In addition, each of the first color filter 16d and the second color filter 16e is a band pass filter transmitting light of a desired wavelength band. Preferably, the pupil filter 16 is disposed inside the observation optical system 17 such that the thin film 16a is positioned on the subject side, and the first color filter 16d and the second color filter 16e are positioned on the imaging device 8c side.

Figure 4:
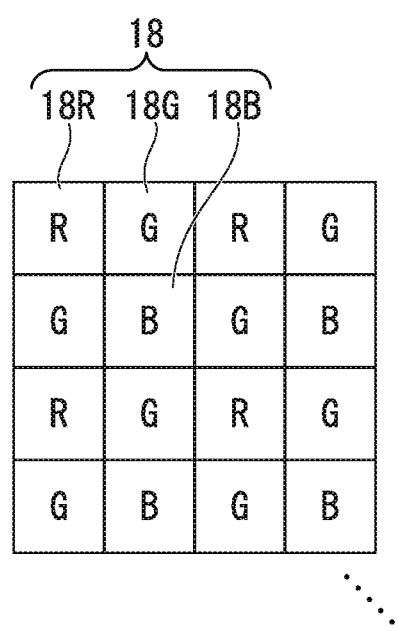
FIG. 4 is a diagram showing the pixel arrangement of an imaging device included in the measurement apparatus according to the first embodiment of the present invention.

FIG. 4 shows the pixel arrangement of the imaging device 8c. The imaging device 8c includes a plurality of pixels 18 disposed in a two-dimensional matrix pattern. Light transmitted through the first pupil 161 of the pupil filter 16 and light transmitted through the second pupil 162 of the pupil filter 16 are incident to the plurality of pixels 18. The plurality of pixels 18 include R pixels 18R, G pixels 18G, and B pixels 18B. Each of the pixels 18 includes a color filter and a photoelectric conversion device. The color filter of each of the pixels 18 is a color filter of an absorption type containing a pigment.

A red filter is disposed on the surface of each R pixel 18R. The R pixel 18R generates a pixel signal based on red light, in other words, an R signal. A green filter is disposed on the surface of each G pixel 18G. The G pixel 18G generates a pixel signal based on green light, in other words, a G signal. A blue filter is disposed on the surface of each B pixel 18B. The B pixel 18B generates a pixel signal based on blue light, in other words, a B signal. The arrangement of the plurality of pixels 18 shown in FIG. 4 is a Bayer array. In the Bayer array, a basic array is disposed regularly and periodically in a row direction and a column direction. The basic array includes one R pixel 18R, two G pixels 18G, and one B pixel 18B.

Figure 5:
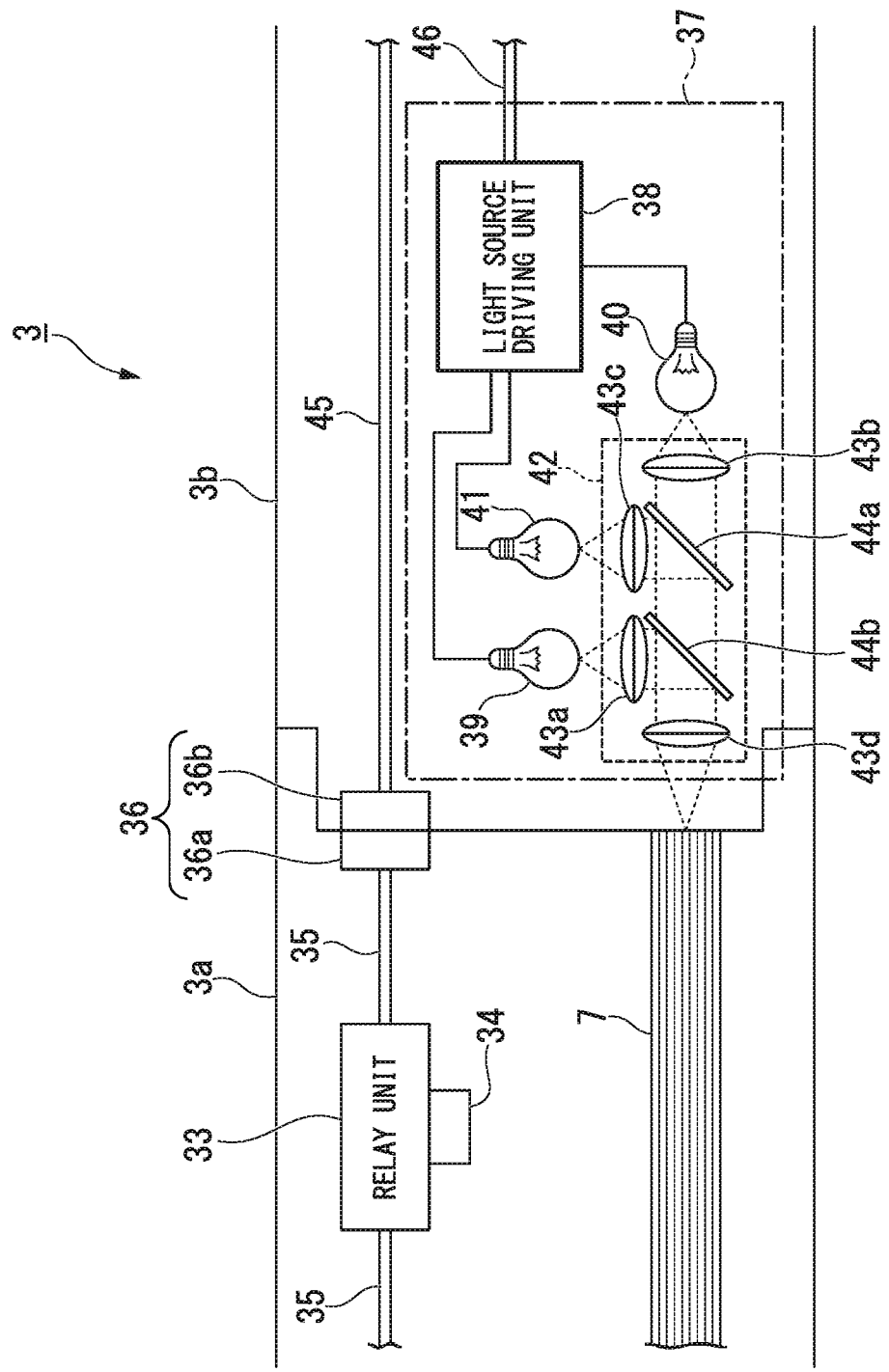
FIG. 5 is a block diagram showing the internal configuration of an operation unit included in the measurement apparatus according to the first embodiment of the present invention.

FIG. 5 shows the internal configuration of the operation unit 3. In the case shown in FIG. 5, the bending operation part 3a and the button operation part 3b constituting the operation unit 3 are connected to each other. A relay unit 33, a scope identifying unit 34, a signal line 35, and a light guide 7 are disposed inside the bending operation part 3a. The relay unit 33 is inserted into the signal line 35. The relay unit 33 amplifies and relays signals transmitted between the imaging device 8c and the apparatus main body 30. The scope identifying unit 34 used for identifying a scope unit 9 is disposed in the relay unit 33. For example, the scope identifying unit 34 is constituted by a resistor having a resistance value that is different for each type of scope unit 9.

The signal line 35 is connected to a signal line 45 disposed inside the button operation part 3b through a connector 36. The signal line 35 and the signal line 45 connect the imaging device 8c and the apparatus main body 30. Each of the signal line 35 and the signal line 45 is a bundle of a plurality of signal lines. Each of the signal line 35 and the signal line 45 includes a signal line that transmits a control signal used for controlling the imaging device 8c to the imaging device 8c. Each of the signal line 35 and the signal line 45 includes a signal line that transmits a pixel signal output from the imaging device 8c to the apparatus main body 30. Each of the signal line 35 and the signal line 45 includes a signal line that transmits a signal output from the scope identifying unit 34 to the apparatus main body 30. Each of the signal line 35 and the signal line 45 may include a signal line having other functions.

The connector 36 includes a first connector 36a disposed inside the bending operation part 3a and a second connector 36b disposed inside the button operation part 3b. The first connector 36a and the second connector 36b are connected to each other. The signal line 35 is connected to the first connector 36a. The signal line 45 is connected to the second connector 36b.

A light source unit 37 constituting a light source is disposed inside the button operation part 3b. The light source unit 37 includes a light source driving unit 38, a red light emitting device 39, a green light emitting device 40, a blue light emitting device 41, and an optical mixing unit 42.

The light source driving unit 38 controls states of the red light emitting device 39, the green light emitting device 40, and the blue light emitting device 41. The light source driving unit 38 is connected to the apparatus main body 30 through the signal line 46. The light source driving unit 38 controls each light emitting device on the basis of a control signal supplied from the apparatus main body 30 through the signal line 46. The light source driving unit 38 supplies electric power to each light emitting device and turns on each light emitting device.

Each of the red light emitting device 39, the green light emitting device 40, and the blue light emitting device 41 is a light emitting device such as a light emitting diode (LED) or a laser diode (LD). The red light emitting device 39 generates red light. The green light emitting device 40 generates green light. The blue light emitting device 41 generates blue light. Light emitted from each light emitting device is incident to the optical mixing unit 42.

The optical mixing unit 42 includes a lens 43a, a lens 43b, a lens 43c, a lens 43d, a dichroic mirror 44a, and a dichroic mirror 44b. The lens 43a parallelizes light emitted from the red light emitting device 39. Light transmitted through the lens 43a is incident to the dichroic mirror 44b. The lens 43b parallelizes light emitted from the green light emitting device 40. Light transmitted through the lens 43b is incident to the dichroic mirror 44a. The lens 43c parallelizes light emitted from the blue light emitting device 41. Light transmitted through the lens 43c is incident to the dichroic mirror 44a.

The dichroic mirror 44a is disposed in optical paths of the light transmitted through the lens 43b and the light transmitted through the lens 43c. The dichroic mirror 44a reflects the light transmitted through the lens 43c and transmits the light transmitted through the lens 43b. Accordingly, the dichroic mirror 44a mixes the light emitted from the green light emitting device 40 and the light emitted from the blue light emitting device 41. The light reflected by the dichroic mirror 44a and the light transmitted through the dichroic mirror 44a are incident to the dichroic mirror 44b.

The dichroic mirror 44b is disposed in optical paths of the light transmitted through the lens 43a, the light reflected by the dichroic mirror 44a, and the light transmitted through the dichroic mirror 44a. The dichroic mirror 44b reflects the light transmitted through the lens 43a and transmits the light emitted from the dichroic mirror 44a. Accordingly, the dichroic mirror 44b mixes the light emitted from the red light emitting device 39, the light emitted from the green light emitting device 40, and the light emitted from the blue light emitting device 41. Illumination light including the light reflected by the dichroic mirror 44b and the light transmitted through the dichroic mirror 44b are incident to the lens 43d. The lens 43d outputs the illumination light to the light guide 7. The light guide 7 transfers the illumination light emitted from the optical mixing unit 42 to the tip end portion 2a.

Figure 6:
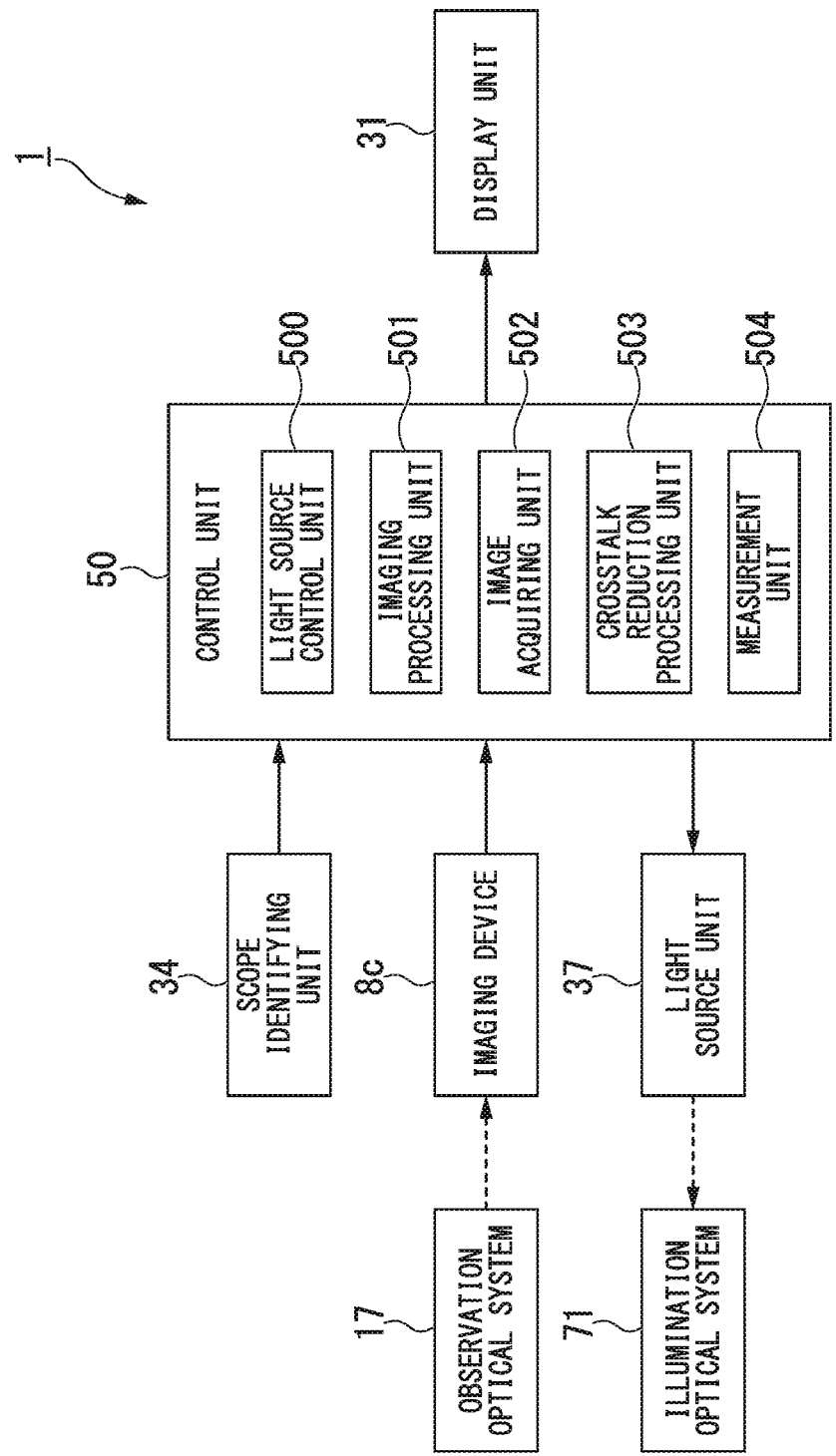
FIG. 6 is a block diagram showing the functional configuration of a measurement apparatus according to the first embodiment of the present invention.

FIG. 6 shows the functional configuration of the measurement apparatus 1. As shown in FIG. 6, the measurement apparatus 1 includes an observation optical system 17, an illumination optical system 71, a scope identifying unit 34, an imaging device 8c, a light source unit 37, a control unit 50, and a display unit 31.

The observation optical system 17 includes the first pupil 161 and the second pupil 162 shown in FIG. 3B. The first pupil 161 is capable of transmitting red light (first light) of a red wavelength band (first wavelength band). The second pupil 162 is capable of transmitting blue light (second light) of a blue wavelength band (second wavelength band) different from the red wavelength band. The first pupil 161 transmits the red light, and the second pupil 162 transmits the blue light. In addition, the first pupil 161 and the second pupil 162 transmit green light of green wavelength bands different from the red wavelength band and the blue wavelength band. The wavelength bands of the green light transmitted by the first pupil 161 and the green light transmitted by the second pupil 162 are different from each other. The first pupil 161 cuts off blue light. In other words, the first pupil 161 does not transmit the blue light. The second pupil 162 cuts off red light. In other words, the second pupil 162 does not transmit the red light.

The observation optical system 17 is constituted as a monocular optical system and includes the pupil filter 16 shown in FIG. 3B. As shown in FIGS. 3A and 3B, the pupil filter 16 includes the flat plate 16f, the thin film 16a, the first pupil 161, and the second pupil 162. The thin film 16a is disposed on the surface of the transparent flat plate 16f. A first opening portion 16b and a second opening portion 16c are formed in the thin film 16a. The first pupil 161 is constituted by the first color filter 16d (third optical filter) shown in FIG. 3A. The first color filter 16d is disposed at the first opening portion 16b and transmits red light. The first color filter 16d is disposed over or in the first opening portion 16b. The second pupil 162 is constituted by the second color filter 16e (fourth optical filter) shown in FIG. 3A. The second color filter 16e is disposed at the second opening portion 16c and transmits blue light. The second color filter 16e is disposed over or in the second opening portion 16c. In addition, the first color filter 16d and the second color filter 16e transmit green light of green wavelength bands different from the red wavelength band and the blue wavelength band. The wavelength bands of the green light transmitted by the first color filter 16d and the green light transmitted by the second color filter 16e are different from each other. The first color filter 16d cuts off blue light. The second color filter 16e cuts off red light.

The scope identifying unit 34 outputs a signal used for identifying a scope unit 9.

The imaging device 8c is disposed at a position to which light transmitted through the observation optical system 17 is incident. As shown in FIG. 4, the imaging device 8c includes a plurality of pixels 18 to which red light that has been transmitted through the first pupil 161 and blue light that has been transmitted through the second pupil 162 are incident. Green light that has been transmitted through the first pupil 161 and the second pupil 162 is incident to a plurality of pixels 18. The plurality of pixels 18 include R pixels 18R (first pixels) and B pixels 18B (second pixels). A red filter (first optical filter) that is capable of transmitting red light (third light) of a red wavelength band (third wavelength band) is disposed in each R pixel 18R. The red filter transmits red light. The R pixel 18R generates an R signal (first pixel signal) based on red light transmitted through the red filter.

A blue filter (second optical filter) that is capable of transmitting blue light (fourth light) of a blue wavelength band (fourth wavelength band) different from the red wavelength band is disposed in each B pixel 18B. The blue filter transmits blue light. The B pixel 18B generates a B signal (second pixel signal) based on blue light transmitted through the blue filter.

The plurality of pixels 18 include G pixels 18G A green filter that is capable of transmitting green light of a green wavelength band different from the red wavelength band and the blue wavelength band is disposed in each G pixel 18G. The green filter transmits green light. The G pixel 18G generates a G signal (third pixel signal) based on green light transmitted through the green filter. The imaging device 8c outputs a Bayer image constituted by an R signal, a G signal, and a B signal.

The light source unit 37 (light source) outputs illumination light including only red light (fifth light) of a red wavelength band (fifth wavelength band) and blue light (sixth light) of a blue wavelength band (sixth wavelength band) not overlapping with the red wavelength band (fifth wavelength band). In addition, the light source unit 37 outputs illumination light including green light of a green wavelength band different from the red wavelength band and the blue wavelength band in addition to the red light and the blue light. Here, two wavelength bands not overlapping with each other represent that the longest wavelength of one wavelength band of which wavelengths are shorter than the shortest wavelength of the other wavelength band.

As shown in FIG. 5, the light source unit 37 includes a red light emitting device 39 (first light emitting device) generating red light and a blue light emitting device 41 (second light emitting device) generating blue light. In addition, the light source unit 37 includes a green light emitting device 40 generating green light.

The illumination optical system 71 emits illumination light emitted from the light source unit 37 to a subject. The light source unit 37 includes an optical mixing unit 42 (optical mixing optical system) shown in FIG. 5. The optical mixing unit 42 mixes red light emitted from the red light emitting device 39 and blue light emitted from the blue light emitting device 41. The optical mixing unit 42 outputs illumination light including the red light and the blue light that have been mixed. In addition, the optical mixing unit 42 mixes green light emitted from the green light emitting device 40, the red light, and the blue light. The optical mixing unit 42 outputs illumination light including the green light, the red light, and the blue light that have been mixed.

As shown in FIG. 1, the measurement apparatus 1 includes the insertion part 2 to be inserted into a subject. The illumination optical system 71 includes a light guide 7 that transfers illumination light transmitted from the optical mixing unit 42 to a tip end of the insertion part 2, in other words, the tip end portion 2a. The light guide 7 functions as an optical transmission unit (optical transmission optical system).

The control unit 50 controls each unit inside the measurement apparatus 1. The control unit 50 includes a light source control unit 500, an imaging processing unit 501, an image acquiring unit 502, a crosstalk reduction processing unit 503, and a measurement unit 504.

The light source control unit 500 controls the state of the light source unit 37. More specifically, the light source control unit 500 sets a mode (state) of the light source unit 37 when the light source unit 37 outputs illumination light to one of a two-color lighting mode and a white lighting mode. When the two-color lighting mode is set in the light source unit 37, the light source unit outputs illumination light including red light and blue light. At this time, the light source control unit 500 turns on the red light emitting device 39 and the blue light emitting device 41 and turns off the green light emitting device 40. On the other hand, when the white lighting mode is set in the light source unit 37, the light source unit 37 outputs illumination light including red light, green light, and blue light, in other words, white light. At this time, the light source control unit 500 turns on the red light emitting device 39, the green light emitting device 40, and the blue light emitting device 41.

The imaging processing unit 501 acquires a Bayer image generated by the imaging device 8c from the imaging device 8c. The Bayer image generated by the imaging device 8c includes an R signal (first pixel signal), a B signal (second pixel signal), and a G signal (third pixel signal).

The image acquiring unit 502 acquires an R image (first image) based on the R signal and a B image (second image) based on the B signal from the Bayer image (captured image) based on the R signal and the B signal. More specifically, the image acquiring unit 502 acquires an R image and a B image from the Bayer image based on the R signal, the G signal, and the B signal.

The crosstalk reduction processing unit 503 corrects a value based on an overlapping component between transmittance characteristics of the R filter in the R pixel 18R and transmittance characteristics of the B filter in the B pixel 18B for the R image. In addition, the crosstalk reduction processing unit 503 corrects a value based on an overlapping component between transmittance characteristics of the R filter in the R pixel 18R and transmittance characteristics of the B filter in the B pixel 18B for the B image. In this way, the crosstalk reduction processing unit 503 generates an R image and a B image in which a component according to crosstalk is reduced. The crosstalk is based on light that passes through the first pupil 161 and arrives at the B pixel 18B and light that passes through the second pupil 162 and arrives at the R pixel 18R.

The measurement unit 504 measures a phase difference (disparity) between the R image and the B image. The measurement unit 504 calculates a subject distance or a three-dimensional shape of a subject based on the phase difference. For example, in a case in which one arbitrary point of an image is designated by a user, the measurement unit 504 calculates a subject distance that is a three-dimensional distance from the tip end portion 2a to the subject. In a case in which two arbitrary points of an image are designated by a user, the measurement unit 504 can calculate a three-dimensional distance between the two points. The measurement unit 504 may calculate the area of a region surrounded by three or more points or the like. The measurement unit 504 may generate three-dimensional point cloud data from a distribution of phase differences of pixels within a rectangular area on an image that is designated by a user.

The display unit 31 is a monitor (display) such as a liquid crystal display (LCD). The display unit 31 may be a touch panel. In such a case, the operation unit 3 and the display unit 31 are integrated. Some or all of functions that can be executed by operations for the button operation part 3b may be executed from the display unit 31.

Each of the light source control unit 500, the imaging processing unit 501, the image acquiring unit 502, the crosstalk reduction processing unit 503, and the measurement unit 504 may be constituted by at least one of a processor and a logic circuit. For example, the processor is at least one of a CPU, a digital signal processor (DSP), and a graphics processing unit (GPU). For example, the logic circuit is at least one of an application specific integrated circuit (ASIC) and a field-programmable gate array (FPGA). Each of the light source control unit 500, the imaging processing unit 501, the image acquiring unit 502, the crosstalk reduction processing unit 503, and the measurement unit 504 may include one or a plurality of processors. Each of the light source control unit 500, the imaging processing unit 501, the image acquiring unit 502, the crosstalk reduction processing unit 503, and the measurement unit 504 may include one or a plurality of logic circuits.

A computer of the measurement apparatus 1 may read a program including commands defining the operations of the light source control unit 500, the imaging processing unit 501, the image acquiring unit 502, the crosstalk reduction processing unit 503, and the measurement unit 504 and execute the read program. In other words, the functions of the light source control unit 500, the imaging processing unit 501, the image acquiring unit 502, the crosstalk reduction processing unit 503, and the measurement unit 504 may be realized by software. The program, for example, may be provided using a "computer-readable recording medium" such as a flash memory. In addition, the program described above may be transmitted from a computer including a storage device or the like in which the program is stored to the measurement apparatus 1 through a transmission medium or using a transmission wave in a transmission medium. Here, the "transmission medium" transmitting the program is a medium having a function of transmitting information such as a network (communication network) including the Internet or a communication circuit line (communication line) including a telephone line. In addition, the program described above may realize a part of the functions described above. Furthermore, the program described above may be a differential file (differential program) that can realize the functions described above by being combined with a program that is already recorded in a computer.

Figure 7:
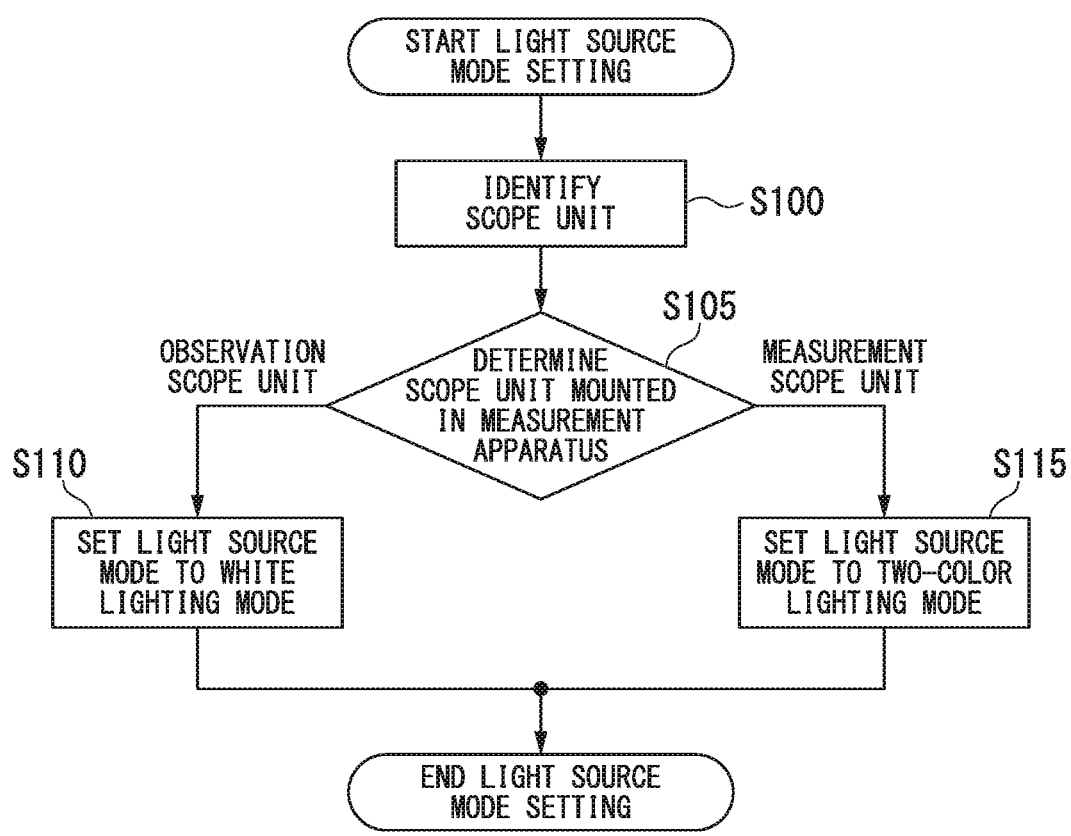
FIG. 7 is a flowchart showing the sequence of light source mode setting according to the first embodiment of the present invention.

FIG. 7 shows the sequence of light source mode setting. The operation of the measurement apparatus 1 in the light source mode setting will be described with reference to FIG. 7. The process of the light source mode setting, for example, is executed immediately after detection of a connection of the bending operation part 3a to the button operation part 3b.

After the light source mode setting is started, the light source control unit 500 identifies a scope unit 9 mounted in the measurement apparatus 1 on the basis of a signal supplied from the scope identifying unit 34 (Step S100).

After, Step S100, the light source control unit 500 determines a scope unit 9 mounted in the measurement apparatus 1 on the basis of a result of the identification of the scope unit 9 (Step S105).

In a case in which the light source control unit 500 determines that an observation scope unit is mounted in the measurement apparatus 1 in Step S105, the light source control unit 500 sets the light source mode of the light source unit 37 to the white lighting mode. In such a case, the light source control unit 500 turns on the red light emitting device 39, the green light emitting device 40, and the blue light emitting device 41 through the light source driving unit 38 (Step S110). When the process of Step S110 is executed, the light source mode setting ends.

On the other hand, in a case in which the light source control unit 500 determines that a measurement scope unit is mounted in the measurement apparatus 1 in Step S105, the light source control unit 500 sets the light source mode of the light source unit 37 to the two-color lighting mode. In such a case, the light source control unit 500, through the light source driving unit 38, turns on the red light emitting device 39 and the blue light emitting device 41 and turns off the green light emitting device 40 (Step S115). When the process of Step S115 is executed, the light source mode setting ends.

For example, in a case in which the white lighting mode is set in the light source unit 37, a live image is displayed on the display unit 31, and measurement is not executed. On the other hand, in a case in which the two-color lighting mode is set in the light source unit 37, measurement is executed as below.

Figure 8:
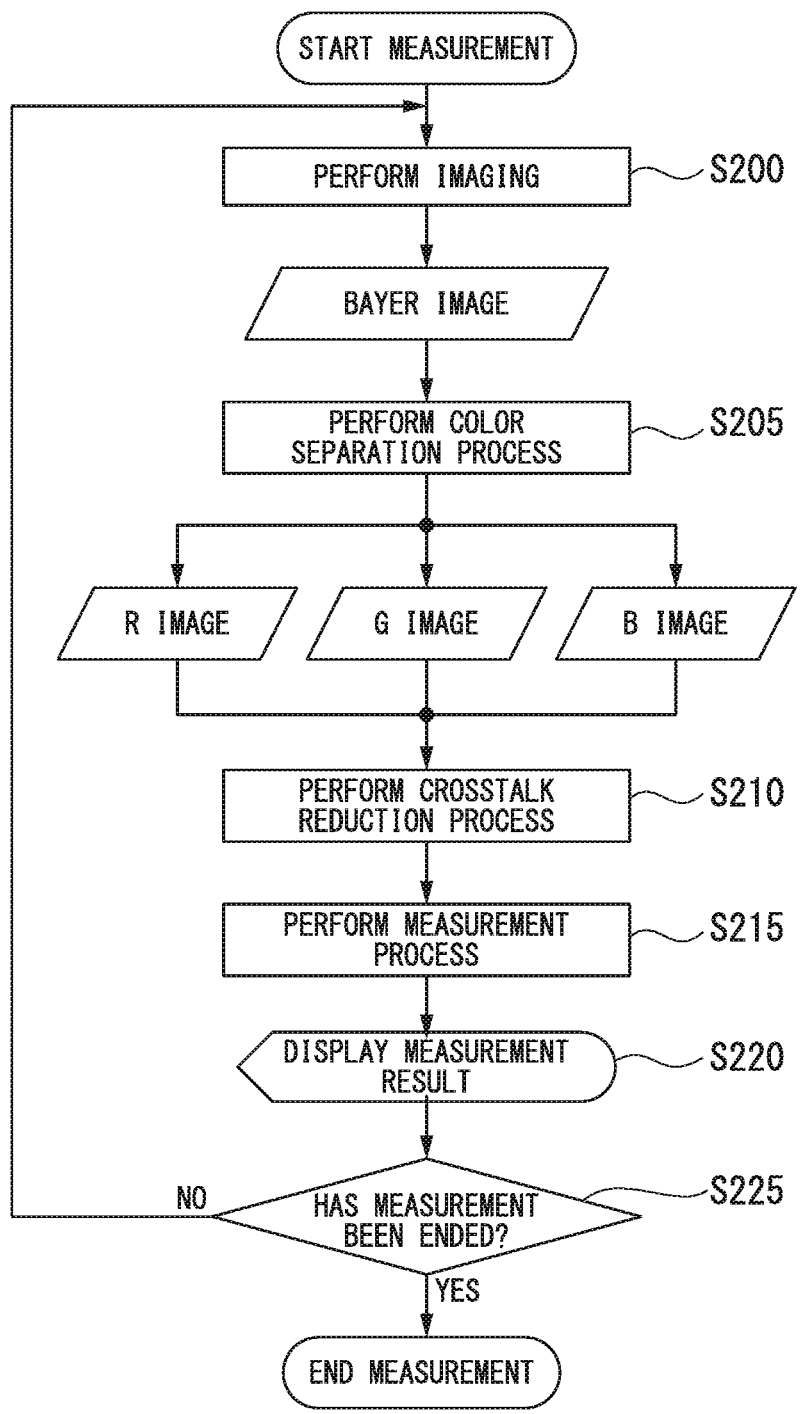
FIG. 8 is a flowchart showing the sequence of measurement according to the first embodiment of the present invention.

FIG. 8 shows the sequence of the measurement. The operation of the measurement apparatus 1 in the measurement will be described with reference to FIG. 8. In a case in which the measurement scope unit is mounted in the measurement apparatus 1, a process shown in FIG. 8 is executed. At this time, the light source mode of the light source unit 37 is the two-color lighting mode.

After the measurement is started, the imaging device 8*c* performs imaging. Accordingly, the imaging device 8*c* generates a Bayer image constituted by an R signal, a G signal, and a B signal. The imaging processing unit 501 acquires the Bayer image from the imaging device 8*c* (Step S200).

After Step S200, the image acquiring unit 502 executes a color separation process (demosaic process), thereby acquiring an R image, a G image, and a B image from the Bayer image (Step S205).

After Step S205, the crosstalk reduction processing unit 503 executes a crosstalk reduction process. Accordingly, the crosstalk reduction processing unit 503 generates an R image and a B image in which a component according to a crosstalk is reduced (Step S210).

After Step S210, the measurement unit 504 executes a measurement process. Accordingly, the measurement unit 504 measures a phase difference between the R image and the B image for which the crosstalk reduction process has been executed. For example, the measurement unit 504 calculates a phase difference between the R image and the B image at a set measurement point. In addition, the measurement unit 504 calculates a subject distance or a three-dimensional shape of a subject on the basis of the phase difference (Step S215).

In Step S215, the control unit 50 may output at least one of the R image and the B image, for which the crosstalk reduction process has been executed, to the display unit 31. The display unit 31 may display at least one of the R image and the B image. For example, the display unit 31 displays the R image.

After Step S215, the control unit 50 outputs a result of the measurement to the display unit 31. The display unit 31 displays the result of the measurement (Step S220). The process of Step S220 is not essential.

After Step S220, the control unit 50 determines whether or not the control unit 50 ends the measurement. For example, the control unit 50 performs a determination on the basis of the state of the scope unit 9. In a case in which a measurement scope unit is mounted in the measurement apparatus 1, the control unit 50 determines that the measurement does not end. In a case in which the measurement scope unit is separated from the measurement apparatus 1, the control unit 50 determines that the measurement ends (Step S225).

In a case in which the control unit 50 determines that the measurement does not end in Step S225, the process of Step S200 is executed. On the other hand, in a case in which the control unit 50 determines that the measurement ends in Step S225, the measurement ends.

By executing the crosstalk reduction process, a measurement error decreases, and the measurement accuracy is improved. In addition, by executing the crosstalk reduction process, the image quality of the R image or the B image displayed at the time of measurement is improved. However, the crosstalk reduction process is not essential. Accordingly, the R image and the B image generated in Step S205 may be used in Step S215. The crosstalk reduction processing unit 503 is not essential.

An image quality improving process such as a γ correction, a scaling process, edge enhancement, or a low pass filter process may be performed for the R image and the B image processed by the crosstalk reduction processing unit 503. A bi-cubic, nearest neighbor, and the like are used in the scaling process. In the low pass filter process, fold-back distortion (aliasing) is corrected.

Details of the color separation process executed by the image acquiring unit 502 will be described. FIG. 9 shows a pixel array of a Bayer image output from the imaging device 8*c*. In each odd-numbered row, red (R) pixels and green (Gr) pixels are alternately disposed. In addition, in each even-numbered row, green (Gb) pixels and blue (B) pixels are alternately disposed. In each odd-numbered column, a red (R) pixel and a green (Gb) pixel are alternately disposed. In addition, in each even-numbered column, a green (Gr) pixel and a blue (B) pixel are alternately disposed. A pixel value of R constitutes an R signal. Pixel values of Gr and Gb constitute a G signal. A pixel value of B constitutes a B signal.

The image acquiring unit 502 performs a black level correction (optical black (OB) subtraction) for pixel values of a Bayer image. In addition, the image acquiring unit 502 copies a pixel value of each pixel, thereby generating pixel values of adjacent pixels. Accordingly, an RGB image is generated in which pixel values of colors are aligned in all the pixels. For example, after performing OB subtraction for the pixel value (R_00) of R, the image acquiring unit 502 copies a pixel value (R_00-OB). Accordingly, pixel values of R in Gr, Gb, and B pixels adjacent to the R pixel are interpolated. FIG. 10 shows a pixel array of an R image.

Similarly, after performing OB subtraction for the pixel value (Gr_01) of Gr, the image acquiring unit 502 copies a pixel value (Gr_01-OB). In addition, after performing OB subtraction for the pixel value (Gb_10) of Gb, the image acquiring unit 502 copies a pixel value (Gb_10-OB).

Accordingly, pixel values of G in an R pixel adjacent to the Gr pixel and a B pixel adjacent to a Gb pixel are interpolated. FIG. 11 shows a pixel array of a G image.

Similarly, after performing OB subtraction for the pixel value (B_11) of B, the image acquiring unit 502 copies a pixel value (B_11-OB). Accordingly, pixel values of B in R, Gr, and Gb pixels adjacent to the B pixel are interpolated. FIG. 12 shows a pixel array of a B image.

The image acquiring unit 502 generates the R image, the G image, and the B image using the process described above. A specific method of the demosaic process is not limited to the method described above. A filter process may be performed for each generated image.

The transmittance characteristics of a filter disposed in each of the pupil filter 16 and the pixel 18 will be described. FIGS. 13 to 17 show the transmittance characteristics of each filter. In graphs shown in FIGS. 13 to 17, the horizontal axis represents a wavelength. In the graphs shown in FIGS. 13 to 17, the vertical axis represents relative transmittance of each filter. Each graph of the transmittance represents a value acquired by normalizing a transmittance for each wavelength using a transmittance for a wavelength at which the transmittance of each filter is the maximum. In addition, FIGS. 13, 16, and 17 also represent spectral characteristics of a light source. In the graphs shown in FIGS. 13, 16, and 17, the vertical axis represents a relative intensity of light emitted by the light source. Each graph of the intensity of light represents a value acquired by normalizing the intensity for each wavelength using an intensity for a wavelength at which the intensity of each light emitting device is the maximum.

Figure 13:
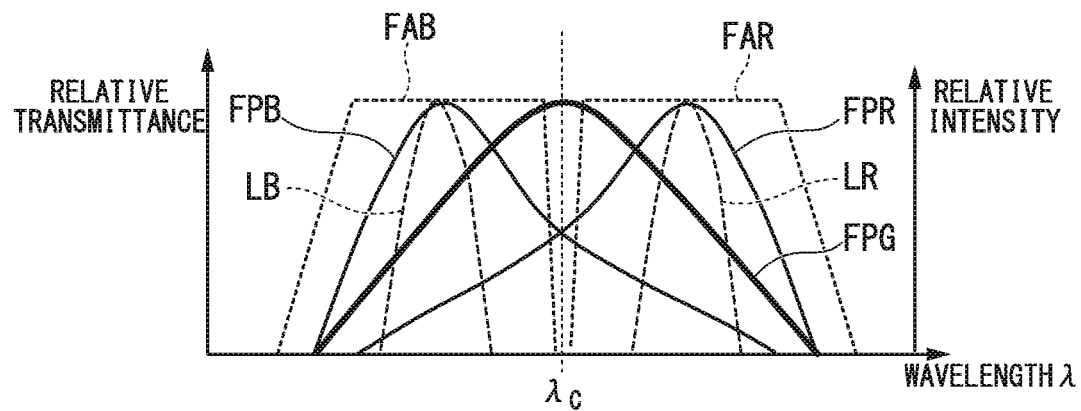
FIG. 13 shows graphs representing transmittance characteristics of each filter and spectral characteristics of a light source according to the first embodiment of the present invention.

In FIG. 13, transmittance characteristics FAR of the first color filter 16d constituting the first pupil 161 and transmittance characteristics FAB of the second color filter 16e constituting the second pupil 162 are shown.

The transmittance characteristics FAR and the transmittance characteristics FAB are different from each other. In other words, the transmission wavelength band (first wavelength band) of the first color filter 16d and the transmission wavelength band (second wavelength band) of the second color filter 16e are different from each other. More specifically, the transmission wavelength band (first wavelength band) of the first color filter 16d is a wavelength band of which wavelengths are longer than a wavelength $\lambda_C$. The transmission wavelength band (second wavelength band) of the second color filter 16e is a wavelength band of which wavelengths are shorter than the wavelength $\lambda_C$. The transmission wavelength band (first wavelength band) of the first color filter 16d and the transmission wavelength band (second wavelength band) of the second color filter 16e do not overlap each other.

The first color filter 16d is a band pass filter transmitting light of a wavelength between a first cutoff wavelength and a second cutoff wavelength. The first cutoff wavelength that is a lower cutoff wavelength of the first color filter 16d is longer than the wavelength $\lambda_C$. The second cutoff wavelength that is an upper cutoff wavelength of the first color filter 16d is longer than the first cutoff wavelength. The second color filter 16e is a band pass filter transmitting light of a wavelength between a third cutoff wavelength and a fourth cutoff wavelength. The fourth cutoff wavelength that is an upper cutoff wavelength of the second color filter 16e is shorter than the wavelength $\lambda_C$. The third cutoff wavelength that is a lower cutoff wavelength of the second color filter 16e is shorter than the fourth cutoff wavelength.

The first color filter 16d may be a long pass filter that has a cutoff wavelength longer than the wavelength $\lambda_C$ and transmits light of a wavelength longer than the cutoff wavelength. The second color filter 16e may be a short pass filter that has a cutoff wavelength shorter than the wavelength $\lambda_C$ and transmits light of a wavelength shorter than the cutoff wavelength. The first color filter 16d may be the long pass filter, and the second color filter 16e may be the short pass filter.

In FIG. 13, transmittance characteristics FPR of a red filter disposed in the R pixel 18R, transmittance characteristics FPG of a green filter disposed in the G pixel 18G, and transmittance characteristics FPB of a blue filter disposed in the B pixel 18B are shown. The transmittance characteristics of the filters overlap each other.

As shown in the transmittance characteristics FPR and the transmittance characteristics FPG, a dominant wavelength of the transmission wavelength band (third wavelength band) of the red filter is longer than a dominant wavelength of the transmission wavelength band of the green filter. As shown in the transmittance characteristics FPG and the transmittance characteristics FPB, a dominant wavelength of the transmission wavelength band of the green filter is longer than a dominant wavelength of the transmission wavelength band (fourth wavelength band) of the blue filter. Accordingly, the dominant wavelength of the transmission wavelength band of the red filter is longer than a dominant wavelength of the transmission wavelength band of the blue filter. The dominant wavelength of each transmission wavelength band is a wavelength at which the transmittance is the maximum in each transmission wavelength band.

At least a part of the transmission wavelength band (first wavelength band) of the first color filter 16d represented by the transmittance characteristics FAR and at least a part of the transmission wavelength band (third wavelength band) of the red filter represented by the transmittance characteristics FPR overlap each other. In the example shown in FIG. 13, the dominant wavelength of the transmittance characteristics FPR is included in the transmission wavelength band of the transmittance characteristics FAR. At least a part of the transmission wavelength band (second wavelength band) of the second color filter 16e represented by the transmittance characteristics FAB and at least a part of the transmission wavelength band (fourth wavelength band) of the blue filter represented by the transmittance characteristics FPB overlap each other. In the example shown in FIG. 13, the dominant wavelength of the transmittance characteristics FPB is included in the transmission wavelength band of the transmittance characteristics FAB.

At least a part of the transmission wavelength band (first wavelength band) of the first color filter 16d represented by the transmittance characteristics FAR and at least a part of the transmission wavelength band of the green filter represented by the transmittance characteristics FPG overlap each other. At least a part of the transmission wavelength band (second wavelength band) of the second color filter 16e represented by the transmittance characteristics FAB and at least a part of the transmission wavelength band of the green filter represented by the transmittance characteristics FPG overlap each other.

In FIG. 13, the spectral characteristics LR of the red light emitting device 39 and the spectral characteristics LB of the blue light emitting device 41 are shown. The wavelength band (fifth wavelength band) of light of the red light emitting device 39 represented by the spectral characteristics LR and the wavelength band (sixth wavelength band) of light of the blue light emitting device 41 represented by the spectral characteristics LB do not overlap each other.

At least a part of the transmission wavelength band (first wavelength band) of the first color filter 16d represented by the transmittance characteristics FAR and at least a part of the transmission wavelength band (fifth wavelength band) of light of the red light emitting device 39 represented by the spectral characteristics LR overlap each other. In the example shown in FIG. 13, the wavelength band (fifth wavelength band) of light of the red light emitting device 39 is included in the transmission wavelength band (first wavelength band) of the first color filter 16d. In the example shown in FIG. 13, the dominant wavelength of the fifth wavelength band is included in the first wavelength band. The transmission wavelength band (first wavelength band) of the first color filter 16d represented by the transmittance characteristics FAR and the wavelength band (sixth wavelength band) of light of the blue light emitting device 41 represented by the spectral characteristics LB do not overlap each other.

At least a part of the transmission wavelength band (second wavelength band) of the second color filter 16e represented by the transmittance characteristics FAB and at least a part of the transmission wavelength band (sixth wavelength band) of light of the blue light emitting device 41 represented by the spectral characteristics LB overlap each other. In the example shown in FIG. 13, the wavelength band (sixth wavelength band) of light of the blue light emitting device 41 is included in the transmission wavelength band (second wavelength band) of the second color filter 16e. In the example shown in FIG. 13, the dominant wavelength of the sixth wavelength band is included in the second wavelength band. The transmission wavelength band (second wavelength band) of the second color filter 16e represented by the transmittance characteristics FAB and the wavelength band (fifth wavelength band) of light of the red light emitting device 39 represented by the spectral characteristics LR do not overlap each other.

The transmission wavelength band (third wavelength band) of the red filter represented by the transmittance characteristics FPR and at least a part of the wavelength band (fifth wavelength band) of light of the red light emitting device 39 represented by the spectral characteristics LR overlap each other. The transmission wavelength band of the green filter represented by the transmittance characteristics FPG and at least a part of the wavelength band (fifth wavelength band) of light of the red light emitting device 39 represented by the spectral characteristics LR overlap each other. The transmission wavelength band (fourth wavelength band) of the blue filter represented by the transmittance characteristics FPB and at least a part of the wavelength band (fifth wavelength band) of light of the red light emitting device 39 represented by the spectral characteristics LR overlap each other. In the example shown in FIG. 13, the wavelength band (fifth wavelength band) of light of the red light emitting device 39 is included in the transmission wavelength band of each of the red filter, the green filter, and the blue filter.

The transmission wavelength band (third wavelength band) of the red filter represented by the transmittance characteristics FPR and at least a part of the wavelength band (sixth wavelength band) of light of the blue light emitting device 41 represented by the spectral characteristics LB overlap each other. The transmission wavelength band of the green filter represented by the transmittance characteristics FPG and at least a part of the wavelength band (sixth wavelength band) of light of the blue light emitting device 41 represented by the spectral characteristics LB overlap each other. The transmission wavelength band (fourth wavelength band) of the blue filter represented by the transmittance characteristics FPB and at least a part of the wavelength band (sixth wavelength band) of light of the blue light emitting device 41 represented by the spectral characteristics LB overlap each other. In the example shown in FIG. 13, the wavelength band (sixth wavelength band) of light of the blue light emitting device 41 is included in the transmission wavelength band of each of the red filter, the green filter, and the blue filter.

Each wavelength in the wavelength band (fifth wavelength band) of light of the red light emitting device 39 represented by the spectral characteristics LR is longer than a dominant wavelength in the transmission wavelength band of the green filter represented by the transmittance characteristics FPG. Each wavelength in the wavelength band (sixth wavelength band) of light of the blue light emitting device 41 represented by the spectral characteristics LB is shorter than a dominant wavelength in the transmission wavelength band of the green filter represented by the transmittance characteristics FPG.

Figure 14:
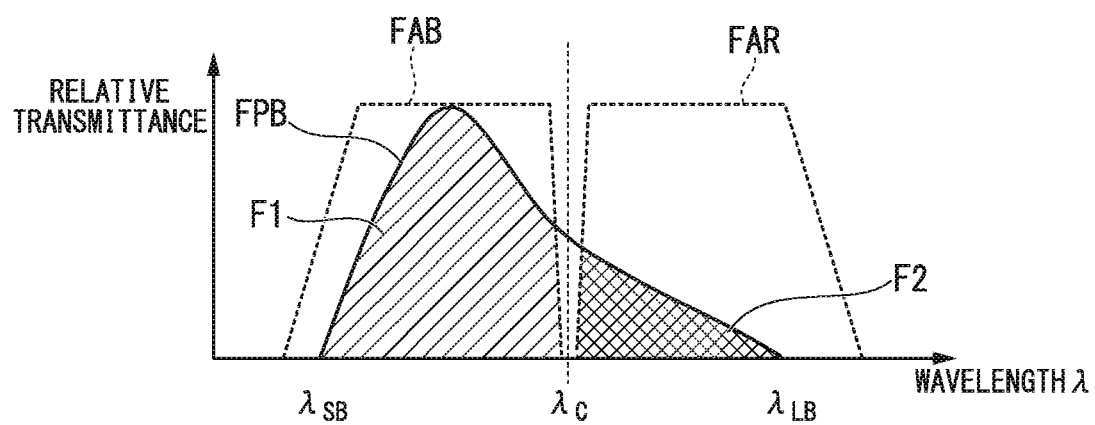
FIG. 14 is a graph representing transmittance characteristics of each filter according to the first embodiment of the present invention.

FIG. 14 shows the transmittance characteristics FAR of the first color filter 16d, the transmittance characteristics FAB of the second color filter 16e, and the transmittance characteristics FPB of the blue filter. In FIG. 14, a transmittance distribution F1 and a transmittance distribution F2 are shown. The transmittance distribution F1 is constituted by each value acquired by multiplying a transmittance in the transmittance characteristics FAB by a transmittance in the transmittance characteristics FPB. The transmittance distribution F2 is constituted by each value acquired by multiplying a transmittance in the transmittance characteristics FAR by a transmittance in the transmittance characteristics FPB.

Figure 15:
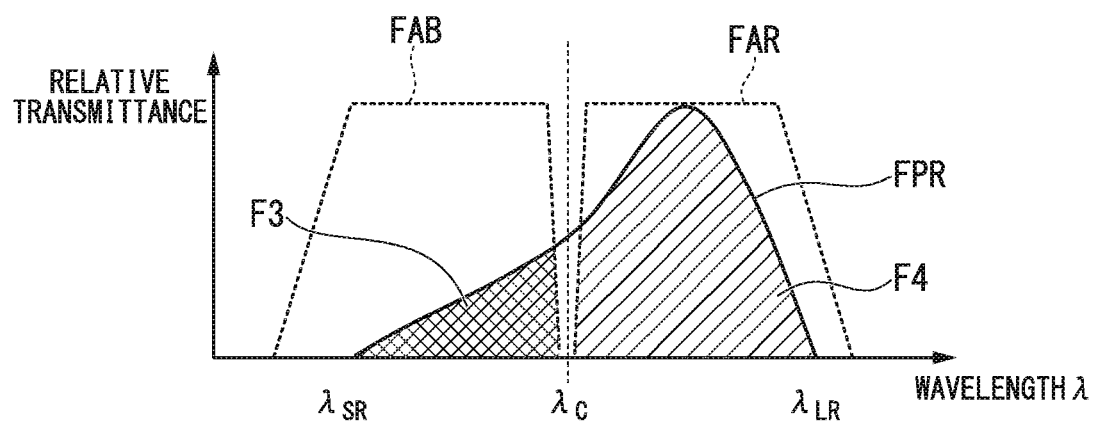
FIG. 15 is a graph representing transmittance characteristics of each filter according to the first embodiment of the present invention.

FIG. 15 shows the transmittance characteristics FAR of the first color filter 16d, the transmittance characteristics FAB of the second color filter 16e, and the transmittance characteristics FPR of the red filter. In FIG. 15, a transmittance distribution F3 and a transmittance distribution F4 are shown. The transmittance distribution F3 is constituted by each value acquired by multiplying a transmittance in the transmittance characteristics FAB by a transmittance in the transmittance characteristics FPR. The transmittance distribution F4 is constituted by each value acquired by multiplying a transmittance in the transmittance characteristics FAR by a transmittance in the transmittance characteristics FPR.

The transmittance wavelength band of the blue filter represented by the transmittance characteristics FPB is from $\mu_{SB}$ to $\lambda_{LB}$. The transmittance wavelength band of the red filter represented by the transmittance characteristics FPR is from $\mu_{SR}$ to $\lambda_{LR}$.

For each wavelength in a wavelength band of which the wavelength is shorter than $\lambda_C$, the transmittance distribution F1 is larger than the transmittance distribution F3. In other words, for each wavelength in a wavelength band of which the wavelength is shorter than 4, the transmittance of a filter constituted by the second color filter 16e and the blue filter is higher than the transmittance of a filter constituted by the second color filter 16e and the red filter.

For each wavelength in a wavelength band of which the wavelength is longer than 4, the transmittance distribution F4 is larger than the transmittance distribution F2. In other words, for each wavelength in a wavelength band of which the wavelength is longer than 4, the transmittance of a filter constituted by the first color filter 16d and the red filter is higher than the transmittance of a filter constituted by the first color filter 16d and the blue filter.

Figure 16:
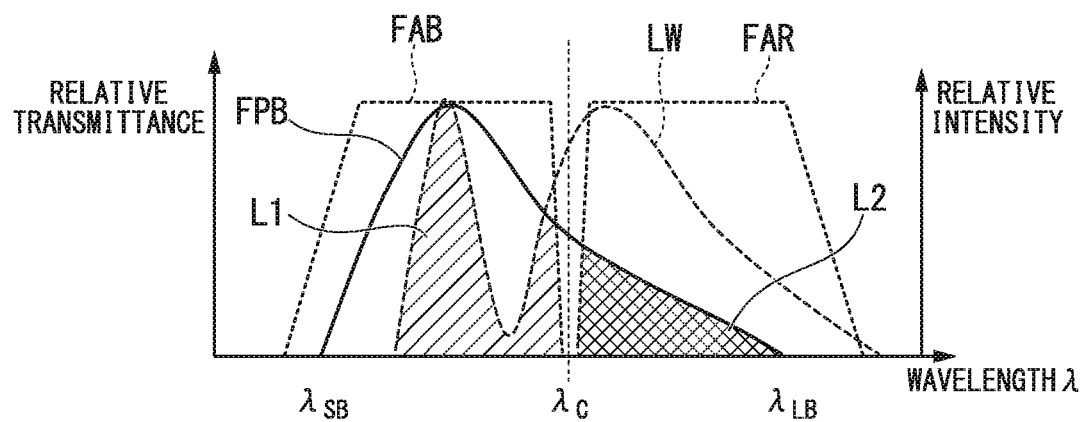
FIG. 16 shows graphs representing transmittance characteristics of each filter and spectral characteristics of a light source according to the first embodiment of the present invention.

FIG. 16 shows the transmittance characteristics FAR of the first color filter 16d, the transmittance characteristics FAB of the second color filter 16e, and the transmittance characteristics FPB of the blue filter. In addition, in FIG. 16, spectral characteristics LW of white light are shown. Furthermore, in FIG. 16, an illumination light component L1 and an illumination light component L2 are shown. The illumination light component L1 represents illumination light transmitted through the second color filter 16e and the blue filter in a case in which the illumination light is white light. The illumination light component L2 represents illumination light transmitted through the first color filter 16d and the blue filter in a case in which the illumination light is white light.

Figure 17:
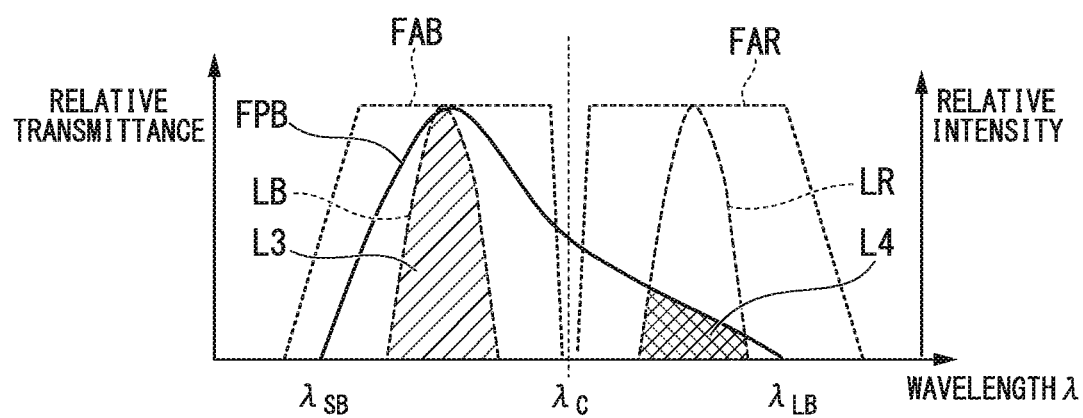
FIG. 17 shows graphs representing transmittance characteristics of each filter and spectral characteristics of a light source according to the first embodiment of the present invention.

FIG. 17 shows the transmittance characteristics FAR of the first color filter 16d, the transmittance characteristics FAB of the second color filter 16e, and the transmittance characteristics FPB of the blue filter. In addition, in FIG. 17, spectral characteristics LR of the red light emitting device 39 and spectral characteristics LB of the blue light emitting device 41 are shown. Furthermore, in FIG. 17, an illumination light component L3 and an illumination light component L4 are shown. The illumination light component L3 represents light of the blue light emitting device 41 transmitted through the second color filter 16e and the blue filter. The illumination light component L4 represents light of the red light emitting device 39 transmitted through the first color filter 16d and the blue filter.

In a B pixel 18B, sum total of the illumination light component L1 and the illumination light component L2 are detected. Alternatively, in the B pixel 18B, sum total of the illumination light component L3 and the illumination light component L4 are detected. The illumination light component L2 and the illumination light component L4 are crosstalk components based on light that passes through the first pupil 161 and arrives at the B pixel 18B. These crosstalk components appear in a B image as crosstalk of the B signal. Since the transmittance characteristics FAR of the first color filter 16d and the transmittance characteristics FPB of the blue filter overlap each other, the illumination light component L2 and the illumination light component L4 are detected in the B pixel 18B. The illumination light component L2 and the illumination light component L4 distorts the waveform of the B image and generates a double-folded image. For this reason, the illumination light component L2 and the illumination light component L4 are not desirable for a B image.

A ratio $S_{L2}/S_{L1}$ of the area $S_{L2}$ of the illumination light component L2 to the area $S_{L1}$ of the illumination light component L1 corresponds to the intensity of crosstalk. Similarly, a ratio $S_{L4}/S_{L3}$ of the area $S_{L4}$ of the illumination light component L4 to the area $S_{L3}$ of the illumination light component L3 corresponds to the intensity of crosstalk. The ratio $S_{L4}/S_{L3}$ is lower than the ratio $S_{L2}/S_{L1}$. In other words, crosstalk is reduced in the two-color lighting mode according to the first embodiment.

Also in the R image, similar to the B image, a component according to crosstalk based on light that passes through the second pupil 162 and arrives at the R pixel 18R is included. The crosstalk is reduced in the two-color lighting mode according to the first embodiment.

In a wavelength band of which the wavelength is shorter than $\lambda_C$, the transmittance characteristics FPG of the green filter and the transmittance characteristics FPR of the red filter generally have a similarity. In addition, in a wavelength band of which the wavelength is longer than $\lambda_C$, the transmittance characteristics FPG of the green filter and the transmittance characteristics FPB of the blue filter generally have a similarity. The crosstalk reduction processing unit 503 executes a crosstalk reduction process using such characteristics. The crosstalk reduction processing unit 503 corrects the R signal and the B signal using Equation (1) and Equation (2) in the crosstalk reduction process.

$$R' = R - \alpha \times G \qquad (1)$$

$$B' = B - \beta \times G \qquad (2)$$

In Equation (1), R represents an R signal before correction, and R' represents an R signal after correction. In Equation (2), B represents a B signal before correction, and B' represents a B signal after correction. In this example, $\alpha$ and $\beta$ are larger than "0" and are smaller than "1." $\alpha$ and $\beta$ are set in accordance with the transmittance characteristics of each filter of the imaging device 8c and the spectral characteristics of a light source. For example, $\alpha$ and $\beta$ are stored in a memory not shown in the drawing.

As described above, in the two-color lighting mode, the light source unit 37 outputs illumination light including only red light and blue light. For this reason, compared to a case in which illumination light is white light, the crosstalk further decreases. The crosstalk reduction processing unit 503 executes a crosstalk reduction process, whereby the crosstalk further decreases. As a result, the measurement apparatus 1 can decrease a measurement error.

When crosstalk occurs, an edge of an image may be easily double-folded. For example, in a case in which the measurement unit 504 performs stereo measurement using an R image and a B image, the measurement unit 504 executes a stereo matching process. In the stereo matching process, a position corresponding to a measurement point designated for one of two images is calculated for the other of the two images. When crosstalk occurs, there are cases in which miss matching occurs in the stereo matching process. In other words, an erroneous position is calculated as a position corresponding to the measurement point. As a result, there are cases in which a measurement error increases. In addition, when crosstalk occurs, a position designated as a measurement point may be incorrect. As a result, there are cases in which a measurement error increases. In the first embodiment, the possibility of increasing such a measurement error decreases.

In observation of a live image, in a case in which the crosstalk reduction process is constantly executed, the image quality of a displayed image is improved. However, the power consumption increases. In the first embodiment, the crosstalk reduction process need not be executed in the observation of a live image. Even in a case in which the crosstalk reduction process is not executed in the observation of a live image, the crosstalk decreases. Since the crosstalk decreases, it is difficult for the edge of an image to be double, and the image quality in the observation of a live image is improved. For this reason, the measurement apparatus 1 can decrease the power consumption.

The crosstalk reduction processing unit 503 may execute the crosstalk reduction process only at the time of measurement.

The measurement apparatus 1 may include a light source unit that includes a white light source and a filter. The light source unit is constituted such that a filter can be inserted in an optical path, and the filter can be withdrawn from the optical path. In the two-color lighting mode, a notch filter cutting off green light included in white light is inserted in the optical path, and thus, illumination light of two colors is generated. In the white lighting mode, the filter is withdrawn from the optical path.

The light source unit 37 need not include the green light emitting device 40. In such a case, only the two-color lighting mode is set in the light source unit 37. In other words, the measurement apparatus 1 that is dedicatedly used for measurement is provided.

The light source unit 37 may include a light emitting device generating blue light as the sixth light and a light emitting device generating green light and red light as the fifth light. In such a case, the first pupil 161 is configured to transmit the green light and the red light and cut off the blue light. The second pupil 162 is configured to transmit the blue light and cut off the green light and the red light. Particularly, a crosstalk component based on light that passes through the second pupil 162 and arrives at the G pixel 18G and the R pixel 18R is reduced. The light emitting device generating the green light and the red light may be constituted by two or more light emitting devices.

The light source unit 37 may include a light emitting device generating blue light and green light as the sixth light and a light emitting device generating red light as the fifth light. In such a case, the first pupil 161 is configured to transmit the red light and cut off the blue light and the green light. The second pupil 162 is configured to transmit the blue light and the green light and cut off the red light. Particularly, a crosstalk component based on light that passes through the first pupil 161 and arrives at the G pixel 18G and the B pixel 18B is reduced. The light emitting device generating the blue light and the green light may be constituted by two or more light emitting devices.

Modified Example of First Embodiment

Figure 18:
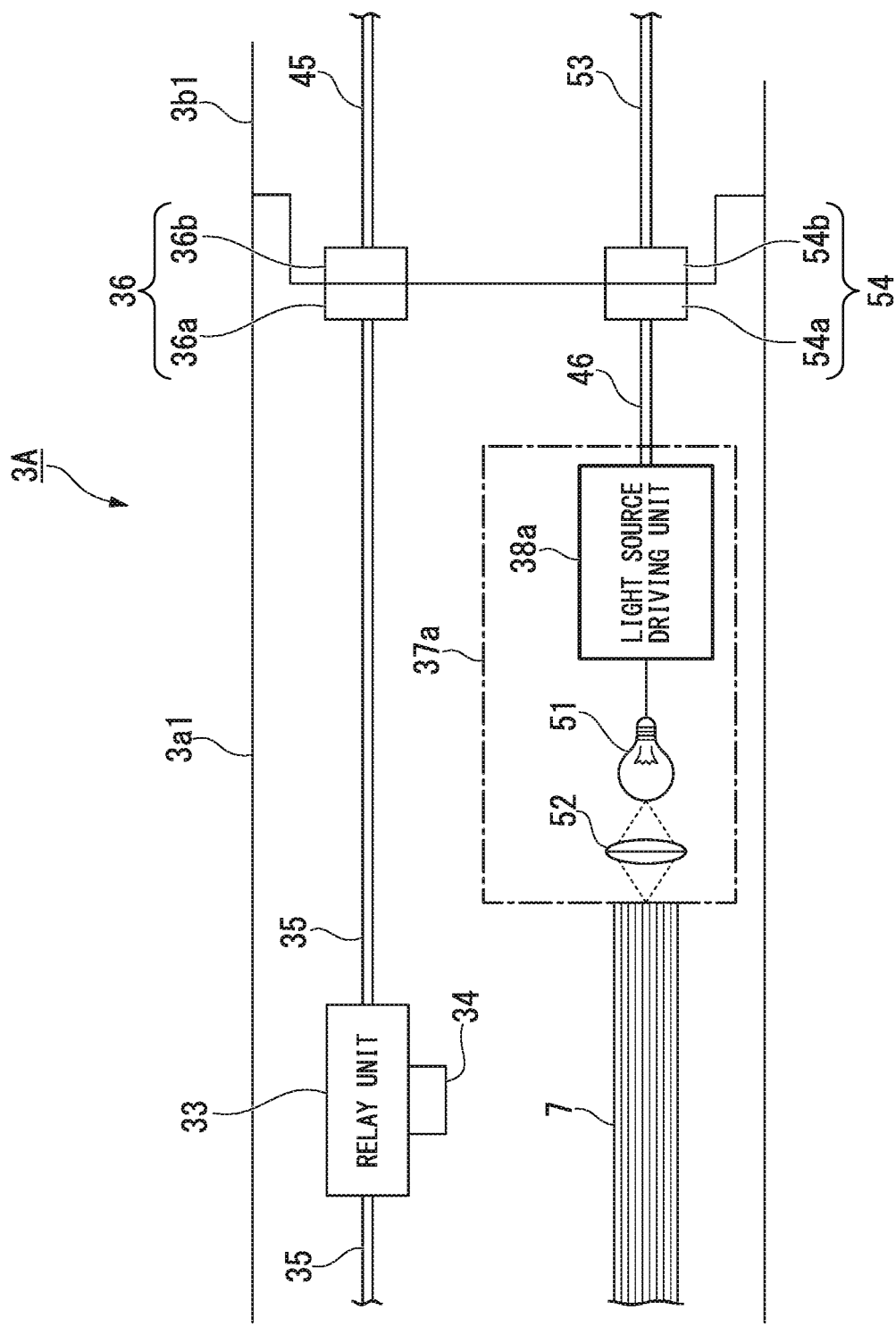
FIG. 18 is a block diagram showing the internal configuration of an operation unit included in a measurement apparatus according to a modified example of the first embodiment of the present invention.
Figure 19:
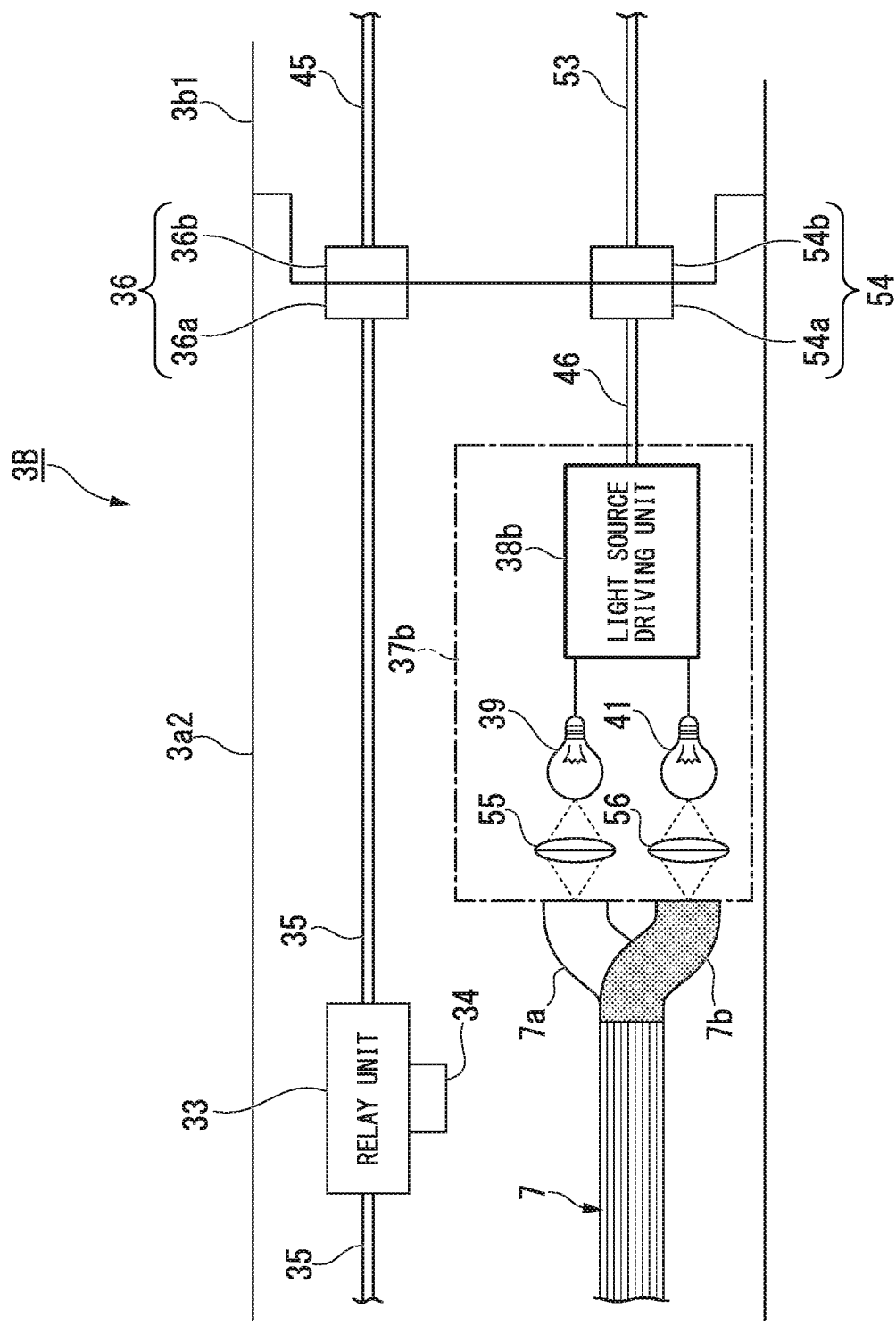
FIG. 19 is a block diagram showing the internal configuration of an operation unit included in the measurement apparatus according to a modified example of the first embodiment of the present invention.

In a modified example of the first embodiment, the operation unit 3 is replaced by an operation unit 3A shown in FIG. 18 and an operation unit 3B shown in FIG. 19. In a configuration shown in FIG. 18, points different from the configuration shown in FIG. 5 will be described.

A bending operation part 3*a*1 and a button operation part 3*b*1 constituting the operation unit 3A are connected to each other. A light source unit 37*a* is disposed inside the bending operation part 3*a*1. An insertion part 2 and the bending operation part 3*a*1 constitutes a scope unit 9. The scope unit 9 includes a light source unit 37*a*. The scope unit 9 in which the light source unit 37*a* is disposed constitutes an observation scope unit.

The light source unit 37*a* includes a light source driving unit 38*a*, a white LED 51, and a lens 52. The light source driving unit 38*a* controls the state of a white LED 51. The white LED 51 generates illumination light of a white color. The illumination light emitted from the white LED 51 is incident to the lens 52. The lens 52 outputs the illumination light to a light guide 7.

A signal line 46 is connected to a signal line 53 disposed inside the button operation part 3*b*1 through a connector 54. The signal line 46 and the signal line 53 connect the light source driving unit 38*a* and the apparatus main body 30. The connector 54 includes a first connector 54*a* disposed inside the bending operation part 3*a*1 and a second connector 54*b* disposed inside the button operation part 3*b*1. The first connector 54*a* and the second connector 54*b* are connected to each other. The signal line 46 is connected to the first connector 54*a*. The signal line 53 is connected to the second connector 54*b*.

In a case in which the light source control unit 500 determines that an observation scope unit is mounted in the measurement apparatus 1 in Step S105 shown in FIG. 7, the light source control unit 500 sets the light source mode of the light source unit 37*a* to the white lighting mode. In such a case, the light source control unit 500 turns on the white LED 51 through the light source driving unit 38*a* (Step S110).

In the configuration shown in FIG. 18, points other than those described above are similar to the configuration shown in FIG. 5.

In the configuration shown in FIG. 19, points different from the configuration shown in FIG. 5 will be described.

The bending operation part 3*a*2 and the button operation part 3*b*1 constituting the operation unit 3B are connected to each other. The light source unit 37*b* is disposed inside the bending operation part 3*a*2. The insertion part 2 and the bending operation part 3*a*2 constitute the scope unit 9. The scope unit 9 includes a light source unit 37*b*. The scope unit 9 in which the light source unit 37*b* is disposed constitute a measurement scope unit. In the light guide 7, an end portion disposed on the button operation part 3*b*1 side branches into a first light guide 7*a* and a second light guide 7*b*. The first light guide 7*a* and the second light guide 7*b* form one bundle on the insertion part 2 side. A plurality of optical fibers constituting the first light guide 7*a* and a plurality of optical fibers constituting the second light guide 7*b* are included in the light guide 7.

The light source unit 37*b* includes a light source driving unit 38*b*, a red light emitting device 39, a blue light emitting device 41, a lens 55, and a lens 56. The light source driving unit 38*b* controls states of the red light emitting device 39 and the blue light emitting device 41. Red light emitted from the red light emitting device 39 is incident to the lens 55. The lens 55 outputs the red light to the first light guide 7*a*. Blue light emitted from the blue light emitting device 41 is incident to the lens 56. The lens 56 outputs the blue light to the second light guide 7*b*.

The signal line 46, the signal line 53, and the connector 54 are respectively the same as the signal line 46, the signal line 53, and the connector 54 shown in FIG. 18.

In a case in which the light source control unit 500 determines that a measurement scope unit is mounted in the measurement apparatus 1 in Step S105 shown in FIG. 7, the light source control unit 500 sets the light source mode of the light source unit 37*b* to the two-color lighting mode. In such a case, the light source control unit 500 turns on the red light emitting device 39 and the blue light emitting device 41 through the light source driving unit 38*b* (Step S115).

In the configuration shown in FIG. 19, points other than those described above are similar to the configuration shown in FIG. 5.

Figure 20:
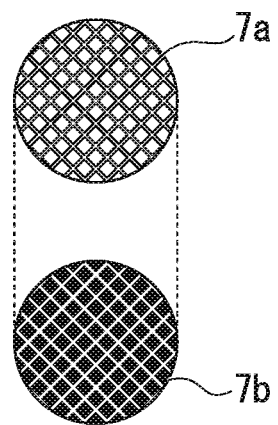
FIG. 20 is a diagram showing end faces of a first light guide and a second light guide included in a measurement apparatus according to a modified example of the first embodiment of the present invention.

FIG. 20 shows end faces of the first light guide 7*a* and the second light guide 7*b* on the button operation part 3*b*1 side. Each of the first light guide 7*a* and the second light guide 7*b* includes a plurality of optical fibers.

Figure 21:
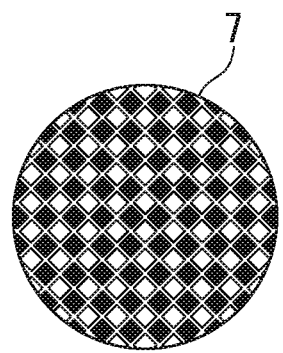
FIG. 21 is a diagram showing an end face of a light guide included in a measurement apparatus according to a modified example of the first embodiment of the present invention.

FIG. 21 shows an end face of the light guides 7 on the tip end portion 2*a* side. Inside the light guide 7, an optical fiber constituting the first light guide 7*a* and an optical fiber constituting the second light guide 7*b* are alternately disposed. The light guide 7 uniformly mixes the red light incident to the first light guide 7*a* and the blue light incident of the second light guide 7*b* on the end face disposed on the tip end portion 2*a* side and emits the illumination light to a subject.

The light guide 7 including the first light guide 7*a* and the second light guide 7*b* and an illumination window 70 constitute an illumination optical system 71 that emits illumination light supplied from the light source unit 37b, which is a light source, to a subject. The illumination optical system 71 includes an optical mixing unit that mixes the red light (fifth light) supplied from the light source unit 37b and the blue light (sixth light) supplied from the light source unit 37b.

The illumination optical system 71 includes a light transmitting unit that transfers illumination light supplied from the optical mixing unit to the tip-end-side of the insertion part 2, that is, a tip end portion 2a. In the example shown in FIG. 19, the light guide 7 constitutes the optical mixing unit and the light transmitting unit. The optical mixing unit and the light transmitting unit may be separated from each other.

Second Embodiment

A second embodiment of the present invention will be described using the measurement apparatus 1 according to the first embodiment. In the first embodiment, crosstalk is reduced, and there are cases in which slight crosstalk remains. There are cases in which it is difficult to determine a fine structure of a subject due to slight crosstalk. An object of a measurement apparatus 1 according to the second embodiment is to resolve crosstalk in an image to be observed.

In the second embodiment, the light source control unit 500 sets the state of the light source unit 37 (light source) to one of a first state and a second state. When the first state is set in the light source unit 37, the light source unit 37 outputs first illumination light including only red light (fifth light) and blue light (sixth light). On the other hand, when the second state is set in the light source unit 37, the light source unit 37 outputs second illumination light including only one of the red light and the blue light. When the second state is set in the light source unit 37, only one of an R image (first image) and a B image (second image) is output to the display unit 31.

In the second embodiment, the light source mode when a measurement scope unit is mounted in the measurement apparatus 1 is set to one of a measurement mode corresponding to the first state and a live observation mode corresponding to the second state. In the measurement mode, the light source unit 37 outputs first illumination light that includes only the red light and the blue light. In the live observation mode, the light source unit 37 outputs second illumination light including only one of the red light and the blue light. A user can direct switching between the light source modes by operating the switch 3d of the operation unit 3.

Figure 22:
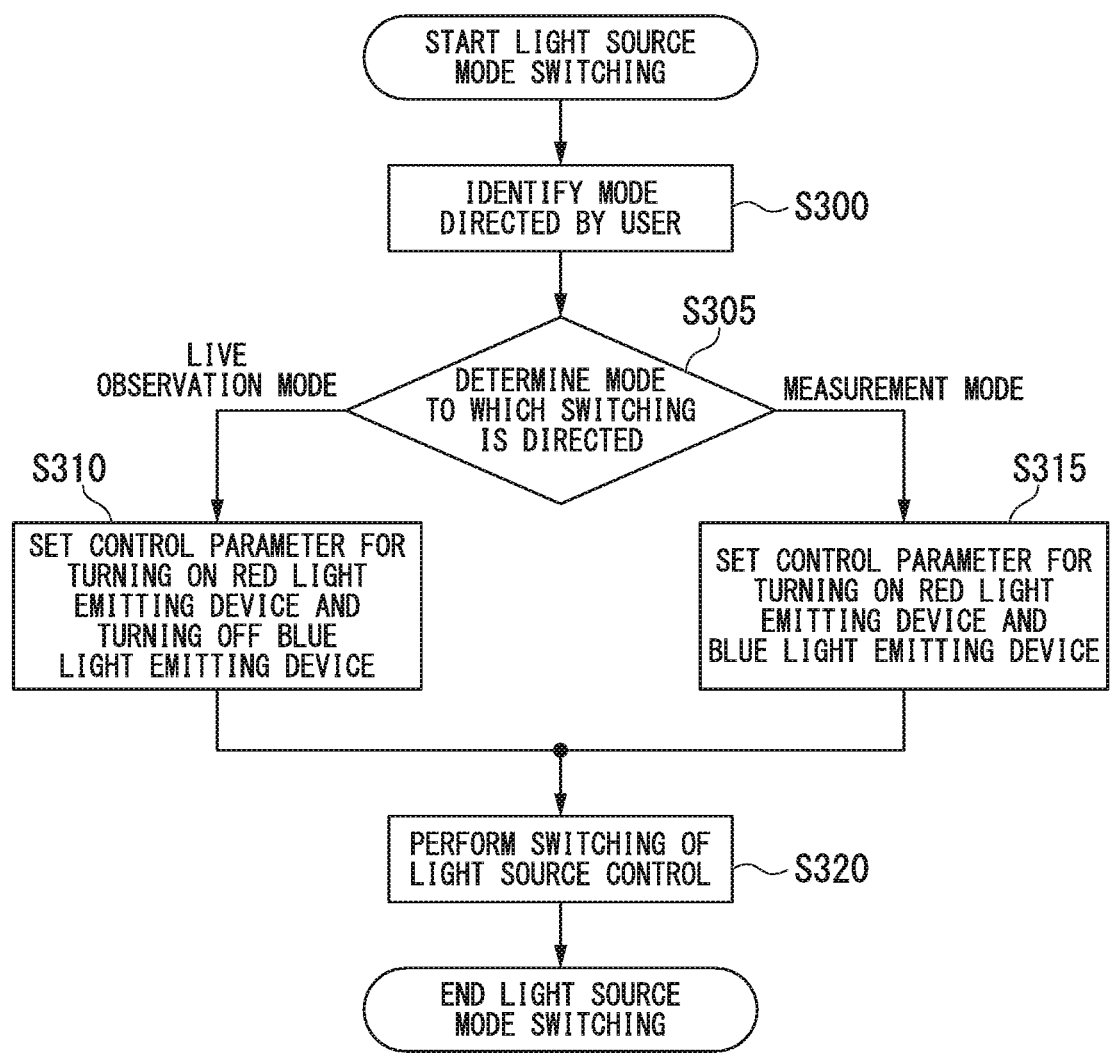
FIG. 22 is a flowchart showing the sequence of light source mode switching according to a second embodiment of the present invention.

FIG. 22 shows the sequence of light source mode switching. When a measurement scope unit is mounted in the measurement apparatus 1, and the switching between the light source modes is directed by a user, light source mode switching is executed. An operation of the measurement apparatus 1 in the light source mode switching will be described with reference to FIG. 22.

After the light source mode switching is started, the light source control unit 500 identifies a mode directed by a user on the basis of a signal supplied from the switch 3d (Step S300).

After Step S300, the light source control unit 500 determines a mode to which switching is directed on the basis of a result of the identification of the mode directed by the user (Step S305).

In a case in which the light source control unit 500 determines that switching to the live observation mode is directed in Step S305, the light source control unit 500 sets the light source mode of the light source unit 37 to the live observation mode. In such a case, the light source control unit 500 sets a control parameter for turning on the red light emitting device 39 and turning off the blue light emitting device 41 in the light source driving unit 38 (Step S310).

After Step S310, the light source control unit 500 switches light source control. In other words, the light source control unit 500 turns on the red light emitting device 39 and turns off the blue light emitting device 41 through the light source driving unit 38 (Step S320). By executing the process of Step S320, the light source mode switching ends.

In a case in which the light source control unit 500 determines that switching to the measurement mode is directed in Step S305, the light source control unit 500 sets the light source mode of the light source unit 37 to the measurement mode. In such a case, the light source control unit 500 sets a control parameter for turning on the red light emitting device 39 and the blue light emitting device 41 in the light source driving unit 38 (Step S315).

After Step S315, the light source control unit 500 switches the light source control. In other words, the light source control unit 500 turns on or turns off the red light emitting device 39 and the blue light emitting device 41 through the light source driving unit 38 on the basis of the control parameter (Step S320). By executing the process of Step S320, the light source mode switching ends.

In a case in which the live observation mode is set in the light source unit 37, the control unit 50 outputs only the R image to the display unit 31 and displays the R image on the display unit 31. The display unit 31 displays the R image.

In a case in which the measurement mode is set in the light source unit 37, the control unit 50 outputs at least one of the R image and the B image to the display unit 31 and displays at least one of the R image and the B image on the display unit 31. The display unit 31 displays at least one of the R image and the B image.

In the live observation mode, the light source control unit 500 may turn on the blue light emitting device 41 and turn off the red light emitting device 39 through the light source driving unit 38. In such a case, only the B image is output to the display unit 31.

A light source mode when an observation scope unit is mounted in the measurement apparatus 1 is a white lighting mode similar to the first embodiment. A light source mode when an observation scope unit is mounted in the measurement apparatus 1 may be the same as the live observation mode described above.

In the live observation mode, since the blue light emitting device 41 is not turned on, a crosstalk component based on light corresponding to the blue light is not incident to the G pixel 18G and the R pixel 18R. For this reason, the crosstalk is resolved. As a result, in the live observation mode, the image quality of an image displayed on the display unit 31 is improved.

In the live observation mode, the blue light emitting device 41 is not turned on. For this reason, a current supplied to the red light emitting device 39 in the live observation mode may be higher than a current supplied to the red light emitting device 39 in the measurement mode. In other words, the light intensity of the second illumination light output by the light source unit 37 when the live observation mode is set in the light source unit 37 may be higher than the light intensity of the first illumination light output by the light source unit 37 when the measurement mode is set in the light source unit 37. Accordingly, in a scene in which the illumination light intensity may be easily insufficient, the S/N of an image displayed on the display unit 31 is improved. For example, a scene in which the illumination light intensity may be easily insufficient is a scene in which a far-located subject is observed or a scene in which a subject having low diffuse reflectance is observed.

Third Embodiment

A third embodiment of the present invention will be described using the measurement apparatus 1 according to the first embodiment. In the first embodiment, in a case in which there is a color deviation in a subject, there are cases in which the S/N of one of an R image and a B image is extremely lower than the S/N of the other of the R image and the B image. For example, in a case in which a subject is rusted in red as a whole, the S/N of a B image is lower than the S/N of an R image. In a case in which a difference in the S/N between the R image and the B image is large, a measurement error may easily increase. An object of a measurement apparatus 1 according to the third embodiment is to prevent an increase in the measurement error in a case in which there is a color deviation in a subject.

In the third embodiment, the light source control unit 500 controls the light intensities of red light (fifth light) generated by the light source unit 37 and blue light (sixth light) generated by the light source unit 37 on the basis of the degree of difference in the brightness between the R image (first image) and the B image (second image). More specifically, the light source control unit 500 performs control of light intensities such that a difference in the brightness between the R image and the B image is decreased. For example, the light source control unit 500 performs control of light intensities such that one of the R image and the B image that is darker than the other is brightened. The light source control unit 500 controls balance of brightness between the R image and the B image.

In the following example, the degree of difference in the brightness between the R image and the B image is represented as a ratio between pixel values of the images. However, the degree of difference in the brightness between the R image and the B image may be represented as a difference between pixel values of the images.

Figure 23:
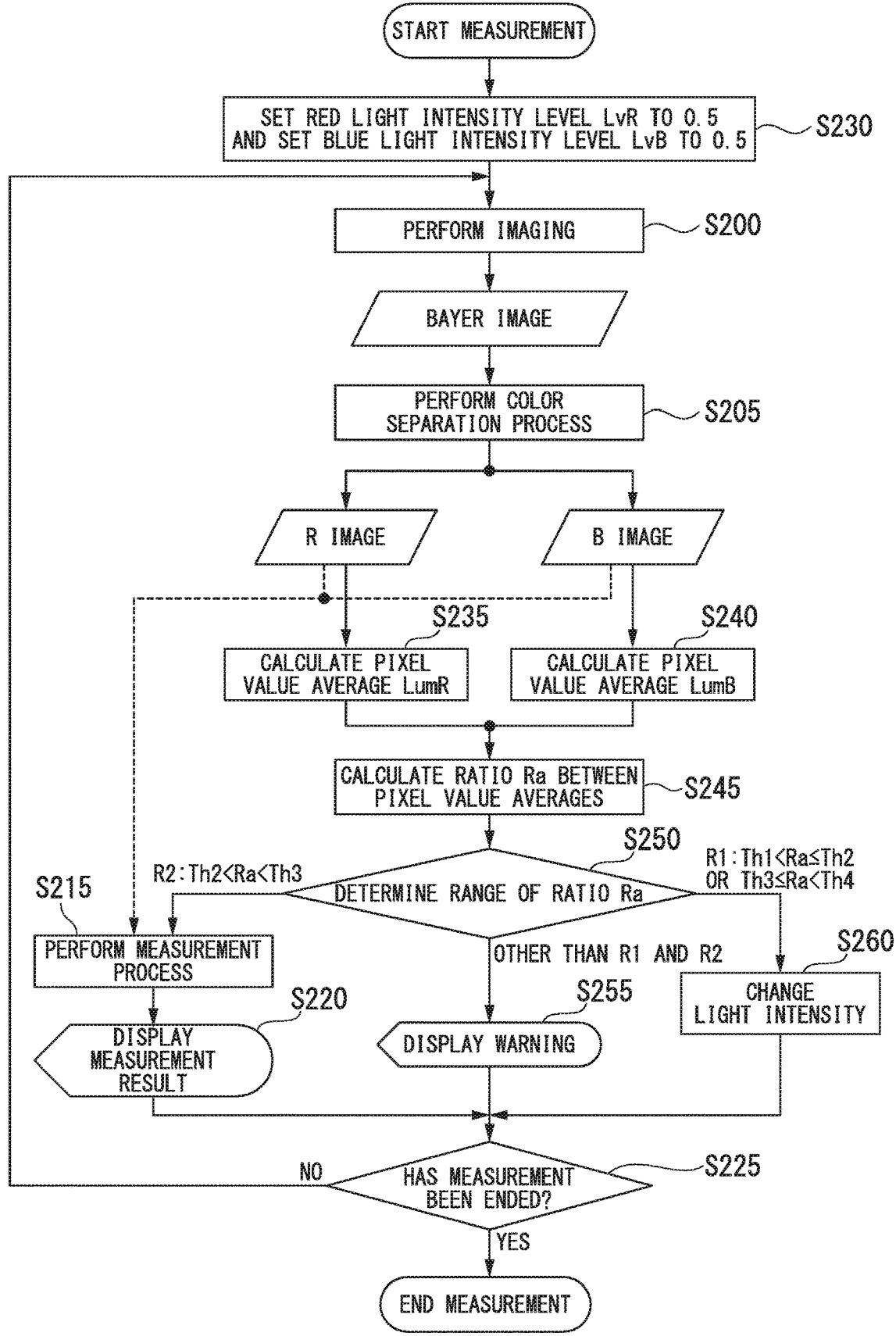
FIG. 23 is a flowchart showing the sequence of measurement according to a third embodiment of the present invention.

FIG. 23 shows the sequence of measurement. In a process shown in FIG. 23, points different from the process shown in FIG. 8 will be described.

After measurement is started, the light source control unit 500 sets a light intensity level in the light source unit 37. More specifically, the light source control unit 500 sets a light intensity level LvR of red light generated by the red light emitting device 39 to 0.5 and sets a light intensity level LvB of blue light generated by the blue light emitting device 41 to 0.5 (Step S230). A sum of the light intensity level LvR and the light intensity level LvB is 1.0. After Step S230, the process of Step S200 is executed.

After Step S205, the light source control unit 500 calculates a pixel value average LumR and a pixel value average LumB (Steps S235 and S240). In Step S235, the light source control unit 500 calculates the pixel value average LumR by averaging pixel values of all or a part of pixels of the R image. In Step S240, the light source control unit 500 calculates the pixel value average LumB by averaging pixel values of all or a part of pixels of the B image.

After Steps S235 and S240, the light source control unit 500 calculates a ratio Ra between the pixel value average LumR and the pixel value average LumB (Step S245). In Step S245, the light source control unit 500 calculates the ratio Ra using Equation (3).

$$Ra = LumR/LumB \quad (3)$$

After Step S245, the light source control unit 500 compares the ratio Ra with predetermined thresholds and determines a range of the ratio Ra. The range R1 is a first range or a second range. The first range is a range in which the ratio Ra is higher than a threshold Th1, and the ratio Ra is a threshold Th2 or less. The second range is a range in which the ratio Ra is a threshold Th3 or more, and the ratio Ra is lower than a threshold Th4. The range R2 is a range in which the ratio Ra is higher than the threshold Th2, and the ratio Ra is lower than the threshold Th3 (Step S250).

For example, the threshold Th1 is 0.25. The threshold Th2 is 0.9. The threshold Th3 is 1.1. The threshold Th4 is 4.0. However, the values of the thresholds are not limited to those of this example. As long as the magnitude relation among the thresholds is maintained, the values of the thresholds may be different from the values described above.

In a case in which the light source control unit 500 determines that the range of the ratio Ra is the range R1 in Step S250, the light source control unit 500 changes the light intensity of the red light generated by the red light emitting device 39 and the light intensity of the blue light generated by the blue light emitting device 41 (Step S260). In Step S260, the light source control unit 500 calculates a light intensity level LvR' after change using Equation (4) and calculates a light intensity level LvB' after change using Equation (5). The light source control unit 500 sets the light intensity level LvR' and the light intensity level LvB' that have been calculated in the light source unit 37. After Step S260, the process of Step S225 is executed.

$$LvR' = LvR/(LvB*Ra + LvR) \quad (4)$$

$$LvB' = LvB*Ra/(LvB*Ra + LvR) \quad (5)$$

In Step S260, the light source control unit 500 performs control of light intensities such that a difference in the brightness between the R image and the B image is decreased. For example, in a case in which the range of the ratio Ra is the first range of the range R1, the B image is brighter than the R image. In such a case, the light source control unit 500 increases the light intensity of the red light emitting device 39 and decreases the light intensity of the blue light emitting device 41, thereby changing the balance of the light intensities of the red light emitting device 39 and the blue light emitting device 41. On the other hand, in a case in which the range of the ratio Ra is the second range of the range R1, the R image is brighter than the B image. In such a case, the light source control unit 500 decreases the light intensity of the red light emitting device 39 and increases the light intensity of the blue light emitting device 41, thereby changing the balance of the light intensities of the red light emitting device 39 and the blue light emitting device 41.

In a case in which the light source control unit 500 determines that the range of the ratio Ra is the range R2 in Step S250, the process of Step S215 is executed. In other words, in a case in which a difference in the brightness between the R image and the B image is small, the measurement unit 504 executes a measurement process.

On the other hand, in a case in which the light source control unit 500 determines that the range of the ratio Ra is a range other than the range R1 and the range R2 in Step S250, the control unit 50 outputs a warning to the display unit 31. The display unit 31 displays the warning (Step S255). In other words, in a case in which a difference in the brightness between the R image and the B image is extremely large, in Step S255, the control unit 50 notifies a user that the subject is not appropriate for measurement. The process of Step S255 is not essential. After Step S255, the process of Step S225 is executed.

In the process shown in FIG. 23, points other than those described above are similar to the process shown in FIG. 8.

In the third embodiment, the light source control unit 500 performs control of the light intensity of the light source unit 37 on the basis of the degree of difference in the brightness between the R image and the B image. The S/N of an image out of the R image and the B image having a lower S/N is improved. For this reason, the measurement apparatus 1 can prevent an increase in the measurement error in the measurement of a subject having a color deviation such as a subject rusted in red as a whole.

In a case in which the degree of difference in the brightness between the R image and the B image is extremely large, the execution of measurement using the measurement unit 504 is avoided. For this reason, the measurement apparatus 1 can avoid a risk of acquiring a result of a large measurement error by executing measurement of a subject such as a subject painted in red or blue that is not appropriate for the measurement based on a phase difference between the R image and the B image.

In a case in which the degree of difference in the brightness between the R image and the B image is extremely high, the control unit 50 displays a warning on the display unit 31. For this reason, the measurement apparatus 1 can notify a user that the subject is not appropriate for measurement.

In Step S255, instead of displaying a warning using the display unit 5, the light source control unit 500 may temporarily set the values of the light intensity level LvR and the light intensity level LvB to values that are three times the values set in Step S260. Accordingly, the light emitting device 39 and the light emitting device 41 emit flash light. In a case in which the degree of difference in the brightness between the R image and the B image is extremely large, the measurement apparatus 1 can acquire an image that is appropriate for measurement.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A measurement apparatus comprising:
    an observation optical system including a first pupil and a second pupil, the first pupil being capable of transmitting first light of a first wavelength band, and the second pupil being capable of transmitting second light of a second wavelength band different from the first wavelength band;
    an imaging device disposed at a position at which light transmitted through the observation optical system is incident and including a plurality of first pixels and a plurality of second pixels, the plurality of first pixels configured to generate first pixel signals based on third light of a third wavelength band transmitted through a first optical filter that is capable of transmitting the third light, the plurality of second pixels configured to generate second pixel signals based on fourth light of a fourth wavelength band transmitted through a second optical filter that is capable of transmitting the fourth light, and the fourth wavelength band being different from the third wavelength band;
    a light source configured to output illumination light including only fifth light of a fifth wavelength band and sixth light of a sixth wavelength band not overlapping the fifth wavelength band; and
    a controller comprising hardware, the controller being configured to:
        acquire a first image based on the first pixel signals and a second image based on the second pixel signals from a captured image based on the first pixel signals and the second pixel signals; and
        measure a phase difference between the first image and the second image,
    wherein the observation optical system comprises a monocular optical system and includes a pupil filter, and
    the pupil filter includes:
        a transparent flat plate;
        a thin film, in which a first opening portion and a second opening portion are formed, disposed on a surface of the flat plate;
        the first pupil comprising a third optical filter disposed at the first opening portion and configured to transmit the first light; and
        the second pupil comprising a fourth optical filter disposed at the second opening portion and configured to transmit the second light,
    at least a part of the first wavelength band and at least a part of the third wavelength band overlap each other,
    at least a part of the first wavelength band and at least a part of the fifth wavelength band overlap each other,
    at least a part of the fifth wavelength band and at least a part of the third wavelength band overlap each other,
    the first wavelength band and the sixth wavelength band do not overlap each other,
    at least a part of the second wavelength band and at least a part of the fourth wavelength band overlap each other,
    at least a part of the second wavelength band and at least a part of the sixth wavelength band overlap each other,
    at least a part of the sixth wavelength band and at least a part of the fourth wavelength band overlap each other, and
    the second wavelength band and the fifth wavelength band do not overlap each other.

2. The measurement apparatus according to claim 1, wherein:
    the controller is further configured to set a state of the light source to one of a first state and a second state,
    the light source is configured to output first illumination light including only the fifth light and the sixth light when the first state is set in the light source,
    the light source is configured to output second illumination light including only one of the fifth light and the sixth light when the second state is set in the light source, and
    only one of the first image and the second image is output to a display when the second state is set in the light source.

3. The measurement apparatus according to claim 1, wherein the controller is further configured to control light intensities of the fifth light and the sixth light on the basis of a degree of difference in brightness between the first image and the second image.

4. The measurement apparatus according to claim 1, wherein the light source includes:
    one or more first light emitting devices configured to generate the fifth light; and one or more second light emitting devices configured to generate the sixth light.

5. The measurement apparatus according to claim 4, further comprising:

an illumination optical system configured to emit the illumination light supplied from the light source to a subject, wherein the light source further includes an optical mixing unit configured to mix the fifth light supplied from the first light emitting device and the sixth light supplied from the second light emitting device and output the illumination light including the fifth light and the sixth light that are mixed.

6. The measurement apparatus according to claim 5, further comprising:

an insertion part to be inserted into the subject, wherein the illumination optical system includes a light guide configured to transfer the illumination light supplied from the optical mixing unit to a tip end of the insertion part.

7. The measurement apparatus according to claim 1, further comprising:

an illumination optical system configured to emit the illumination light supplied from the light source to a subject, wherein the illumination optical system includes an optical mixing unit configured to mix the fifth light supplied from the light source and the sixth light supplied from the light source.

8. The measurement apparatus according to claim 7, further comprising:

an insertion part to be inserted into the subject, wherein the illumination optical system further includes a light guide configured to transfer the illumination light supplied from the optical mixing unit to a tip end of the insertion part.

* * * * *